US011251378B2

(12) United States Patent
Park et al.

(10) Patent No.: US 11,251,378 B2
(45) Date of Patent: Feb. 15, 2022

(54) ORGANIC LIGHT-EMITTING DIODE HAVING ALLEVIATED LUMINANCE REDUCTION IN LOW DYNAMIC RANGE

(71) Applicant: SFC CO., LTD., Cheongju-si (KR)

(72) Inventors: Young-Hwan Park, Cheongju-si (KR); Seo-Yeon Yoon, Seongnam-si (KR); So Young Shim, Daejeon (KR); Chang-Hee Lee, Cheongju-si (KR); Dong-Won Han, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 365 days.

(21) Appl. No.: 15/763,090

(22) PCT Filed: Sep. 13, 2016

(86) PCT No.: PCT/KR2016/010330
§ 371 (c)(1),
(2) Date: Mar. 23, 2018

(87) PCT Pub. No.: WO2017/065415
PCT Pub. Date: Apr. 20, 2017

(65) Prior Publication Data

US 2018/0277771 A1 Sep. 27, 2018

(30) Foreign Application Priority Data

Oct. 13, 2015 (KR) ........................ 10-2015-0142750

(51) Int. Cl.

| | |
|---|---|
| ***H01L 51/00*** | (2006.01) |
| ***C09K 11/06*** | (2006.01) |
| *C07D 307/91* | (2006.01) |
| *C07D 209/86* | (2006.01) |
| *H01L 51/50* | (2006.01) |
| *C07D 209/80* | (2006.01) |
| *H01L 51/52* | (2006.01) |

(52) U.S. Cl.
CPC .......... *H01L 51/0073* (2013.01); *C09K 11/06* (2013.01); *H01L 51/0052* (2013.01); *C07D 209/80* (2013.01); *C07D 209/86* (2013.01); *C07D 307/91* (2013.01); *C09K 2211/1018* (2013.01); *H01L 51/0003* (2013.01); *H01L 51/0058* (2013.01); *H01L 51/0072* (2013.01); *H01L 51/0074* (2013.01); *H01L 51/5012* (2013.01); *H01L 51/5016* (2013.01); *H01L 51/5056* (2013.01); *H01L 51/5068* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01)

(58) Field of Classification Search
CPC ............. H01L 51/0073; H01L 51/0052; H01L 51/0058; H01L 51/0072; C09K 11/06; C09K 2211/1018
See application file for complete search history.

(56) References Cited

U.S. PATENT DOCUMENTS

2015/0053944 A1* 2/2015 Kim .................... H01L 51/0094 257/40

FOREIGN PATENT DOCUMENTS

| | | | | |
|---|---|---|---|---|
| JP | 2010034548 A * | 2/2010 | ............. | C09K 11/06 |
| KR | 1020060022676 A | 3/2006 | | |
| KR | 1020080015865 A | 2/2008 | | |
| KR | 1020120047706 A | 5/2012 | | |

OTHER PUBLICATIONS

International Search Report of PCT/KR2016/010330, dated Dec. 19, 2016, English Translation.

* cited by examiner

*Primary Examiner* — Robert S Jones, Jr.
(74) *Attorney, Agent, or Firm* — STIP Law Group, LLC

(57) ABSTRACT

The present disclosure relates to an organic light-emitting diode which can operate at a low voltage with high efficiency and exhibits the effect of having an alleviated luminance reduction rate in a low dynamic range. More particularly, the organic light-emitting diode comprises: a first electrode; a second electrode facing the first electrode; and a light-emitting layer and a charge balance control layer arranged sequentially between the first and the second electrode, wherein the light-emitting layer includes at least one of amine derivative compounds represented by the following Chemical Formula A and the charge balance control layer includes at least one of anthracene derivative compounds represented by the following Chemical Formula B or C. The structures of Chemical Formulas A, B, and C are as defined in the specification.

7 Claims, 6 Drawing Sheets

ORGANIC LIGHT-EMITTING DIODE HAVING ALLEVIATED LUMINANCE REDUCTION IN LOW DYNAMIC RANGE

CROSS-REFERENCE TO RELATED APPLICATIONS

This application is the U.S. National Phase under 35 U.S.C. § 371 of International Application No. PCT/KR2016/010330 filed on Sep. 13, 2016, which in turn claims the benefit of Korean Application No. 10-2015-0142750, filed on Oct. 13, 2015, the disclosures of which are incorporated by reference into the present application.

TECHNICAL FIELD

The present disclosure relates to an organic light-emitting diode and, more particularly, to an organic light-emitting diode exhibiting an alleviated luminance reduction rate in a low dynamic range, wherein a luminous material having a specific structure is used in a light-emitting layer and a charge balance control layer having a specific structure for increasing the luminance efficiency of the organic light-emitting diode is introduced between the light-emitting layer and an electron injection layer.

BACKGROUND ART

Organic light-emitting diodes, based on self-luminescence, exhibit the advantages of having a wide viewing angle, excellent contrast, fast response time, high brightness, excellent driving voltage, and excellent response rate characteristics and of allowing for a polychromic display.

A typical organic light-emitting diode includes a positive electrode (anode) and a negative electrode (cathode), facing each other, with an organic emission layer disposed therebetween.

As to a general structure of the organic light-emitting diode, a hole transport layer, a light-emitting layer, an electron transport layer, and a cathode are formed in that order on an anode. Here, all of the hole transport layer, the light-emitting layer, and the electron transport layer are organic films comprising organic compounds.

An organic light-emitting diode having such a structure operates as follows: when a voltage is applied between the anode and the cathode, the anode injects holes which are then transferred to the light-emitting layer via the hole transport layer while electrons injected from the cathode move to the light-emitting layer via the electron transport layer. In the luminescent zone, the carriers such as holes and electrons recombine to produce an exciton. When the exciton returns to the ground state from the excited state, the molecule of the light-emitting layer emits light.

Materials used as the organic layers in organic light-emitting diodes may be divided according to functions into luminescent materials and charge carrying materials, for example, a hole injection material, a hole transport material, an electron injection material, and an electron transport material. The light-emitting mechanism forms the basis of classification of luminescent materials as fluorescent and phosphorescent material, which use excitons in singlet and triplet states, respectively.

Meanwhile, when a single material is employed as the luminescent material, intermolecular actions cause the maximum luminescence wavelength to shift toward a longer wavelength, resulting in a reduction in color purity and light emission efficiency due to light attenuation. In this regard, a host-dopant system may be used as a luminescent material so as to increase the color purity and the light emission efficiency through energy transfer. This is based on the principle whereby, when a dopant which is smaller in energy band gap than a host forming a light-emitting layer is added in a small amount to the light-emitting layer, excitons are generated from the light-emitting layer and transported to the dopant, emitting light at high efficiency. Here, light with desired wavelengths can be obtained depending on the kind of the dopant because the wavelength of the host moves to the wavelength range of the dopant.

With regard to related arts pertaining to dopant compounds in the light-emitting layer, reference may be made to Korean Patent No. 10-2008-0015865 A (Feb. 20, 2008), which describes an organic light-emitting diode using an arylamine-coupled indenofluorene derivative, and Korean Patent No. 10-2012-0047706 A (May 14, 2012), which describes an organic photoelectric device using a compound in which dibenzofuran or dibenzothiophene coexists with fluorene or in which benzofuran or dibenzothiophene coexists with carbazole.

Another technique for improving luminance efficiency can be found in Korean Patent No. 10-2006-0022676 A (Mar. 10, 2006), which describes an organic electroluminescence device having a blocking layer, disposed between a light-emitting layer and an electron transport layer, for controlling electron density.

In spite of various efforts made to fabricate organic light-emitting diodes having effective luminescence characteristics, however, each of the elements constituting an organic light-emitting diode is still required to have a minimum change in luminance in order to maximize color reproduction and color expression in a wide dynamic range. Particularly, there is still a continued need to develop organic light-emitting diodes free of the problem of large luminance changes in a low dynamic range (low current), which makes low-voltage driving difficult and causes specific colors to drastically decrease in luminance, resulting in make it difficult to implement stable expression of a white color.

DETAILED DESCRIPTION OF THE INVENTION

Technical Problem

Accordingly, the present disclosure has been made keeping in mind the above problems occurring in the related art, and an object of the present disclosure is to provide an organic light-emitting diode that has an alleviated luminance reduction rate in a low dynamic range.

Technical Solution

The present disclosure provides an organic light-emitting diode comprising: a first electrode; a second electrode facing the first electrode; and a light-emitting layer and a charge balance control layer arranged sequentially between the first and the second electrode, wherein the light-emitting layer includes at least one of amine derivative compounds represented by the following Chemical Formula A and the charge balance control layer includes at least one of anthracene derivative compounds represented by the following Chemical Formula B or C:

[Chemical Formula A]

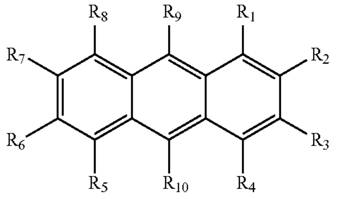

wherein, $R_1$ to $R_{10}$ may be the same or different and are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkyl germanium of 1 to 30 carbon atoms, a substituted or unsubstituted aryl germanium of 6 to 30 carbon atoms, a cyano, a nitro, and a halogen, with a proviso that at least one of $R_1$ to $R_{10}$ is a substituent represented by the following Structural Formula A or B:

[Structural Formula A]

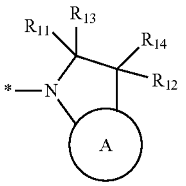

[Structural Formula B]

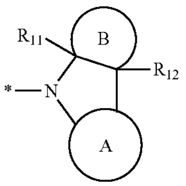

wherein, the ring moiety A is a substituted or unsubstituted aromatic hydrocarbon ring of 6 to 40 carbon atoms, or a substituted or unsubstituted heteroaromatic ring of 3 to 40 carbon atoms, the ring moiety B of Structural Formula B is a substituted or unsubstituted cycloalkylene of 2 to 8 carbon atoms, $R_{11}$ to $R_{14}$ may be the same or different and are each independently selected from the group consisting of a hydrogen atom, a deuterium atom, a substituted or unsubstituted alkyl of 1 to 30 carbon atoms, a substituted or unsubstituted cycloalkyl of 3 to 30 carbon atoms, a substituted or unsubstituted aryl of 6 to 30 carbon atoms, a substituted or unsubstituted heteroaryl of 3 to 30 carbon atoms, a substituted or unsubstituted alkoxy of 1 to 30 carbon atoms, a substituted or unsubstituted aryloxy of 6 to 30 carbon atoms, a substituted or unsubstituted aralkyl of 7 to 30 carbon atoms, a substituted or unsubstituted alkenyl of 2 to 30 carbon atoms, a substituted or unsubstituted alkynyl of 2 to 30 carbon atoms, a cyano, and a halogen,

* denotes a bonding site to the anthracene moiety, and when the anthracene moiety has plural substituents of Structural Formula A or B attached thereon, they may be the same or different; and

[Chemical Formula B]

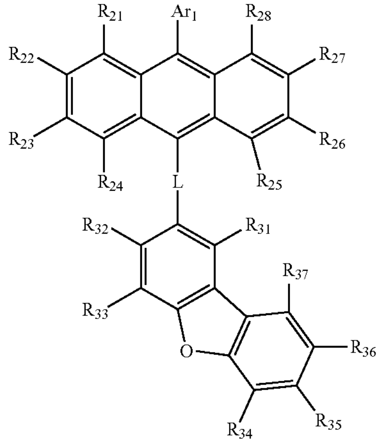

[Chemical Formula C]

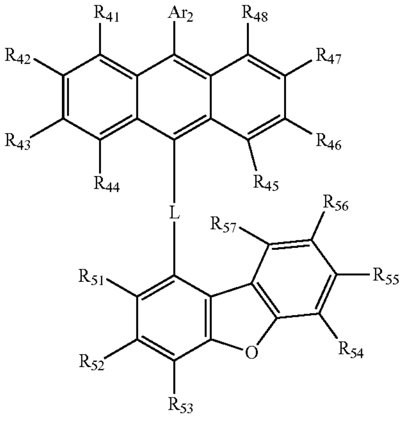

wherein, $R_{21}$ to $R_{28}$, $R_{31}$ to $R_{37}$, $R_{41}$ to $R_{48}$, and $R_{51}$ to $R_{57}$ may be the same or different and are each independently selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, a substituted or unsubstituted silyl of 1 to 30 carbon atoms, a substituted or unsubstituted germanium of 1 to 30 carbon atoms, a substituted or unsubstituted boron of 1 to 30 carbon atoms, a substituted or unsubstituted aluminum of to 30 carbon atoms, a carbonyl, a phosphoryl, an amino, a thiol, a hydroxy, a selenium, a tellurium, an amide, an ether, and an ester, $Ar_1$ and $Ar_2$ are each independently a substituted or unsubstituted aryl of 6 to 50 carbon atoms, or a substituted or unsubstituted heteroaryl of 2 to 50 carbon atoms; and L is a linker selected from among a single bond, a substituted or unsubstituted arylene of 6 to 60 carbon atoms, and a substituted or unsubstituted heteroarylene of 2 to 60 carbon atoms.

Advantageous Effects

Employing a light-emitting layer and a charge balance control layer electron which have specially structured respective materials, the organic light-emitting diode of the present disclosure can exhibit alleviated luminance reduction rates in a low dynamic range, compared to conventional diodes.

BEST MODE FOR INVENTION

Mode for Carrying Out the Invention

Figure 1:
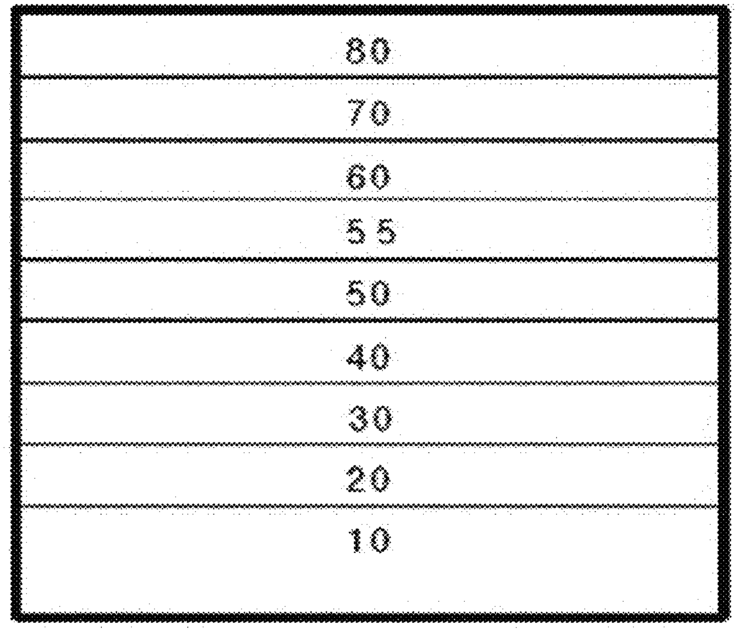
FIG. 1 is a schematic diagram of the structure of an organic light-emitting device according to an embodiment of the present invention.

Hereinafter, some embodiments which can be easily embodied by those skilled in the art will be described with reference to the accompanying drawings. In the drawings of the invention, sizes and dimensions of structures are illustrated by enlargement or reduction thereof as compared with the actual sizes and dimensions to clarify the invention, the known configurations are not illustrated to exhibit characteristic configurations, and the invention is not limited to the drawings.

In elucidating the principles of embodiments of the present disclosure in detail, descriptions of well-known functions and configurations relevant to the present inventive concept will be omitted below if they have been deemed to obscure the gist of the present invention.

In addition, the size and thickness of each configuration illustrated in the drawings are arbitrarily illustrated for the sake of convenience of explanation, and thus the present invention may not be necessarily limited to the illustration. Further, in the drawings, the thickness of layers and regions are illustrated enlarged for clarity. For the sake of explanation, thicknesses of certain layers and regions are exaggerated.

Throughout the specification, when a portion may "include" a certain constituent element, unless explicitly described to the contrary, it may not be construed to exclude another constituent element but may be construed to further include other constituent elements. Further, throughout the specification, the word "on" means positioning on or below the object portion, but does not essentially mean positioning on the lower side of the object portion based on a gravity direction.

The present disclosure provides an organic light-emitting diode comprising: a first electrode; a second electrode facing the first electrode; and a light-emitting layer and a charge balance control layer arranged sequentially between the first and the second electrode, wherein the light-emitting layer includes at least one of amine derivative compounds represented by the following Chemical Formula A and the charge balance control layer includes at least one of anthracene derivative compounds represented by the following Chemical Formula B or C:

[Chemical Formula A]

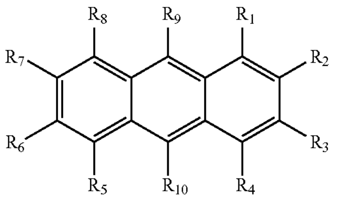

wherein, $R_1$ to $R_{10}$ may be the same or different and are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkyl germanium of 1 to 30 carbon atoms, a substituted or unsubstituted aryl germanium of 6 to 30 carbon atoms, a cyano, a nitro, and a halogen, with a proviso that at least one of $R_1$ to $R_{10}$ is a substituent represented by the following Structural Formula A or B:

[Structural Formula A]

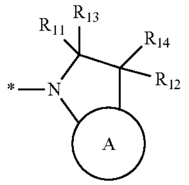

[Structural Formula B]

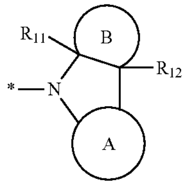

wherein, the ring moiety A is a substituted or unsubstituted aromatic hydrocarbon ring of 6 to 40 carbon atoms, or a substituted or unsubstituted heteroaromatic ring of 3 to 40 carbon atoms, the ring moiety B of Structural Formula B is a substituted or unsubstituted cycloalkylene of 2 to 8 carbon atoms, $R_{11}$ to $R_{14}$ may be the same or different and are each independently selected from the group consisting of a hydrogen atom, a deuterium atom, a substituted or unsubstituted alkyl of 1 to 30 carbon atoms, a substituted or unsubstituted cycloalkyl of 3 to 30 carbon atoms, a substituted or unsubstituted aryl of 6 to 30 carbon atoms, a substituted or unsubstituted heteroaryl of 3 to 30 carbon atoms, a substituted or unsubstituted alkoxy of 1 to 30 carbon atoms, a substituted or unsubstituted aryloxy of 6 to 30 carbon atoms, a substituted or unsubstituted aralkyl of 7 to 30 carbon atoms, a substituted or unsubstituted alkenyl of 2 to 30 carbon atoms, a substituted or unsubstituted alkynyl of 2 to 30 carbon atoms, a cyano, and a halogen,

* denotes a bonding site to the anthracene moiety, and when the anthracene moiety has plural substituents of Structural Formula A or B attached thereon, they may be the same or different; and

[Chemical Formula B]

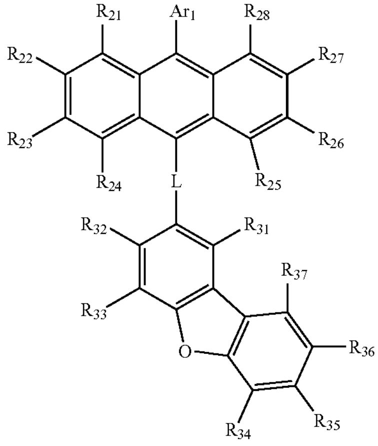

-continued

[Chemical Formula C]

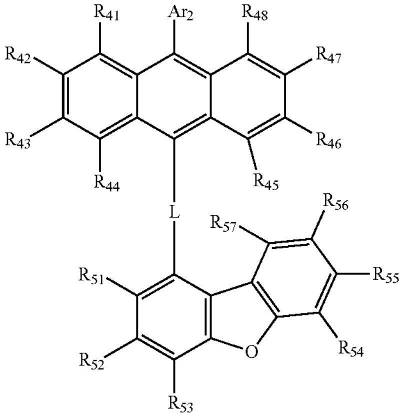

wherein, $R_{21}$ to $R_{28}$, $R_{31}$ to $R_{37}$, $R_{41}$ to $R_{48}$, and $R_{51}$ to $R_{57}$ may be the same or different and are each independently selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, a substituted or unsubstituted silyl of 1 to 30 carbon atoms, a substituted or unsubstituted germanium of 1 to 30 carbon atoms, a substituted or unsubstituted boron of 1 to 30 carbon atoms, a substituted or unsubstituted aluminum of to 30 carbon atoms, a carbonyl, a phosphoryl, an amino, a thiol, a hydroxy, a selenium, a tellurium, an amide, an ether, and an ester, $Ar_1$ and $Ar_2$ are each independently a substituted or unsubstituted aryl of 6 to 50 carbon atoms, or a substituted or unsubstituted heteroaryl of 2 to 50 carbon atoms; and L is a linker selected from among a single bond, a substituted or unsubstituted arylene of 6 to 60 carbon atoms, and a substituted or unsubstituted heteroarylene of 2 to 60 carbon atoms, wherein the term 'substituted' of the expression "substituted or unsubstituted" used with Chemical Formulas A to C means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, an heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms such as in "a substituted or unsubstituted alkyl of 1 to 30 carbon atoms", "a substituted or unsubstituted aryl of 6 to 50 carbon atoms", etc. means the total number of carbon atoms of, for example, the alkyl or aryl radical or moiety alone, exclusive of the number of carbon atoms of the substituent. For instance, a phenyl group with a butyl at the para position falls within the scope of an aryl of 6 carbon atoms although it is substituted with a butyl radical of 4 carbon atoms.

As used herein, the term "aryl" means an organic radical derived from an aromatic hydrocarbon by removing one hydrogen atom and encompasses a 5- to 7-membered and preferably a 5- or 6-membered monocyclic ring or fused ring system. In addition, the aromatic system may further include a fused ring that is formed by adjacent substituents, if present, on the aryl radical.

Examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, but are not limited thereto.

At least one hydrogen atom on the aryl radical may be substituted by a deuterium atom, a halogen atom, a hydroxy, a nitro, a cyano, a silyl, an amino ($—NH_2$, —NH(R), —N(R') (R") wherein R' and R" are each independently an alkyl of 1 to 10 carbon atoms, in this case called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms.

The substituent heteroaryl used in the compound of the present disclosure refers to a cyclic aromatic system of 2 to 24 carbon atoms bearing one to three heteroatoms selected from among N, O, P, Si, S, Ge, Se, and T. In the aromatic system, two or more rings may be fused. One or more hydrogen atoms on the heteroaryl may be substituted by the same substituents as on the aryl.

As used herein, the term "heteroaromatic ring" refers to an aromatic hydrocarbon ring bearing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy used in the compounds of the present disclosure include methoxy, ethoxy, propoxy, sec-butyloxy, iso-amyloxy, hexyloxy. At least one hydrogen atom of the alkoxy may be substituted by the same substituent as in the aryl.

Representative among the silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms in the silyl may be substituted by the same substituent as in the aryl.

In the present disclosure, the phrase "(an organic layer) includes at least one organic compound" may be construed to mean "(an organic layer) may include a single organic compound species or two or more different species of organic compounds falling within the scope of the present disclosure".

In the organic light-emitting diode according to one embodiment of the present disclosure, the first and the second electrode may serve as an anode and a cathode, respectively, and a hole transport layer disposed between the anode and a light-emitting layer and an electron transport layer is disposed between a charge balance control layer and the cathode. In this regard, the organic light-emitting diode of the present disclosure may comprise a hole injection layer between the anode and the hole transport layer and an electron injection layer between the electron transport layer and the cathode.

In addition, the light-emitting layer of the organic light-emitting diode contains a host and a dopant wherein the anthracene compound represented by Chemical Formula A may serve as the dopant.

Using the amine derivative compound represented by Chemical Formula A as a dopant in a light-emitting layer and the anthracene derivative compound represented by Chemical Formula B or C as a material in the charge balance control layer, the organic light-emitting diode according to the present disclosure exhibits alleviated luminance reduction rates in low grayscale areas, compared to conventional organic light-emitting diodes. According to another embodiment of the present disclosure, $R_9$ and $R_{10}$ in Chemical Formula A may be the same or different and are each independently a substituted or unsubstituted aryl of 6 to 18 carbon atoms or a substituted or unsubstituted heteroaryl of 2 to 18 carbon atoms. In this case, the ring moiety A in Structural Formulas A and B may be an aromatic hydrocarbon ring of 6 to 12 carbon atoms.

Further, the anthracene derivative represented by Chemical Formula A may have one or two substituents represented by Structural Formula A or B. In this regard, the substituent represented by Structural Formula A or B may not exist on the carbon atoms for the substituents $R_9$ and $R_{10}$.

In Chemical Formula A, none or one of the substituents $R_1$ to $R_4$ may be the substituent of Structural Formula A or B and none or one of the substituents $R_5$ to $R_8$ may be the substituent of Structural Formula A or B.

Concrete examples of the anthracene derivative represented by Chemical Formula A in the present invention include, but are not limited to, the following Compounds 101 to 145:

<Compound 101>

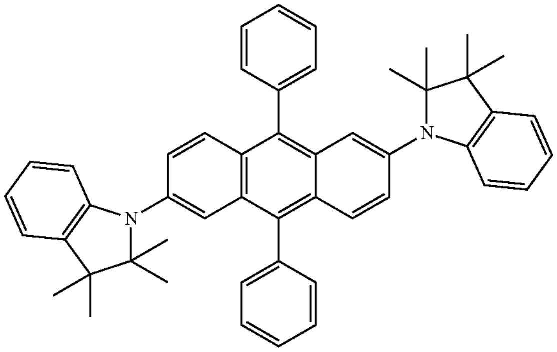

-continued
<Compound 102>
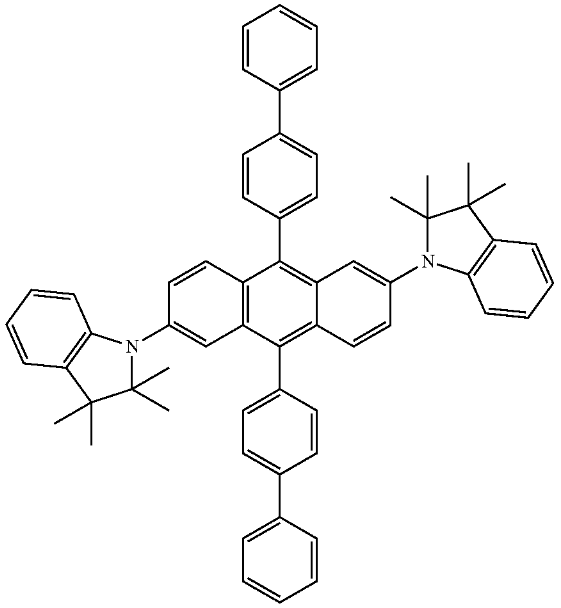
<Compound 103>
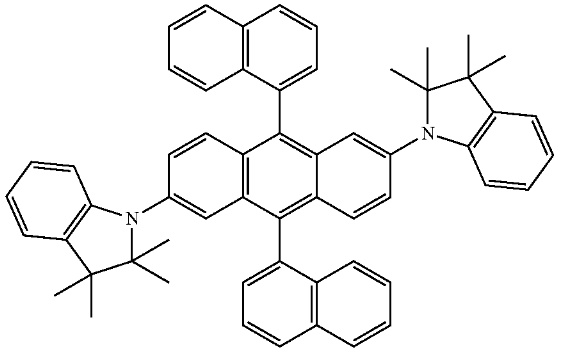
<Compound 104>
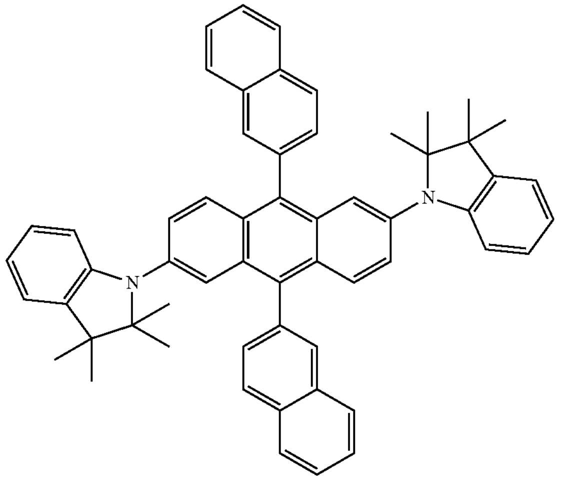
-continued
<Compound 105>
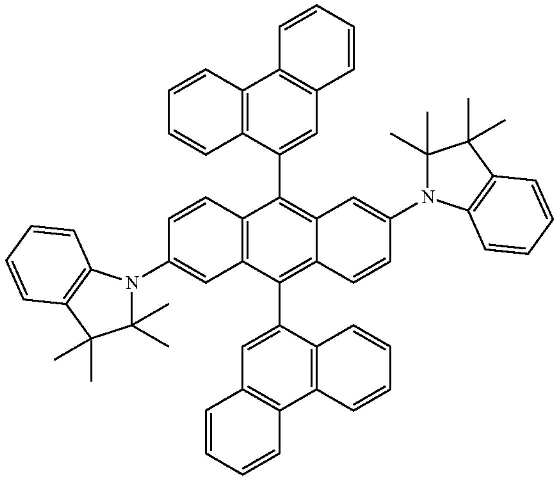
<Compound 106>
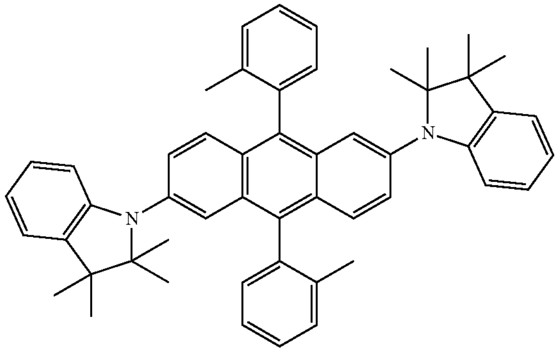
<Compound 107>
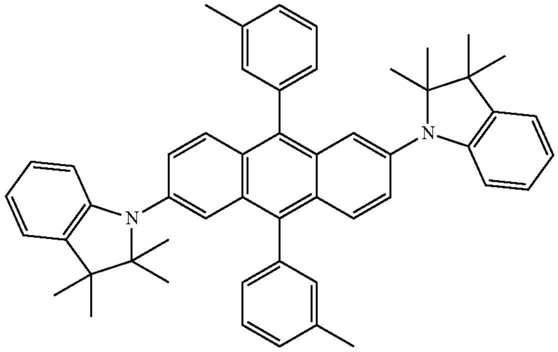

-continued
<Compound 108>
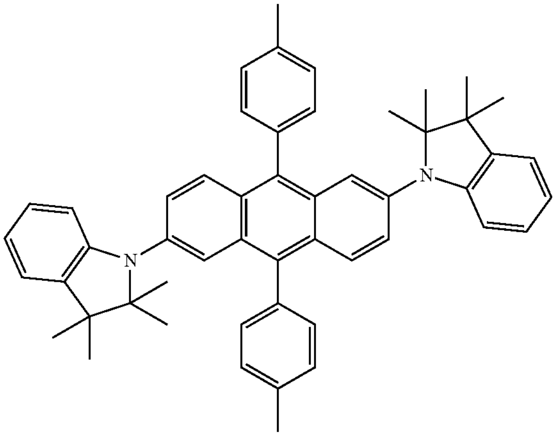
<Compound 109>
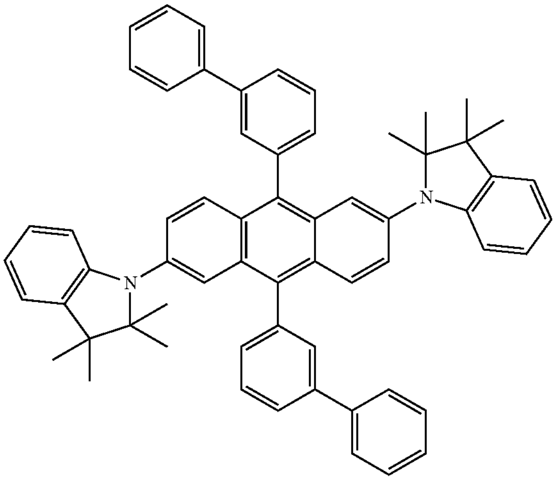
<Compound 110>
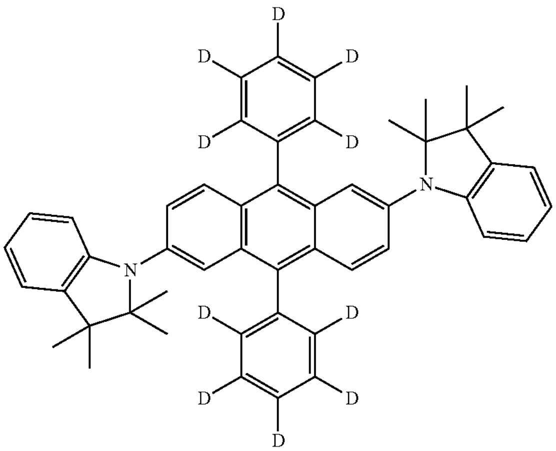
-continued
<Compound 111>
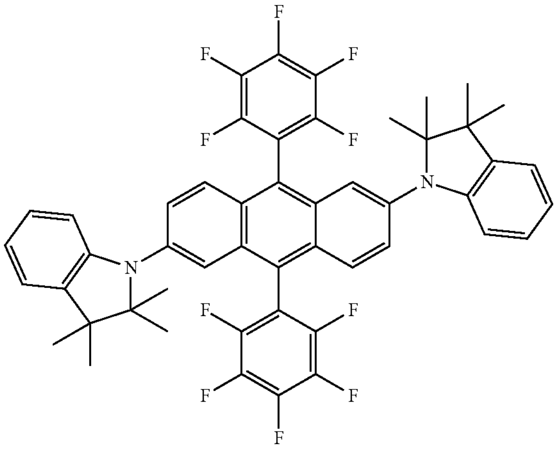
<Compound 112>
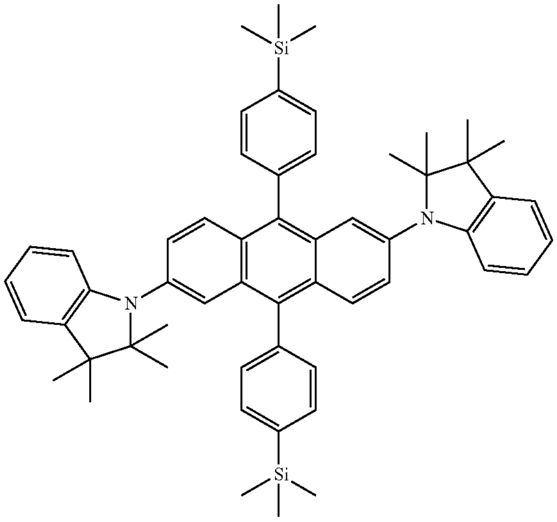
<Compound 113>
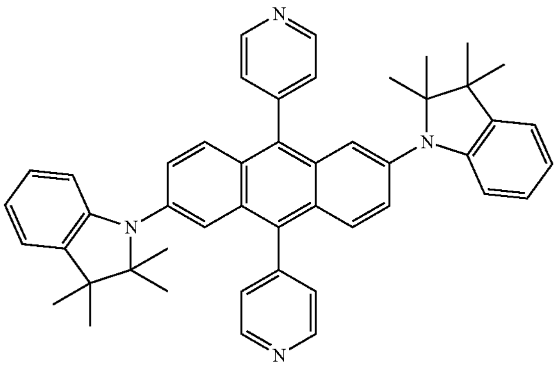

-continued
<Compound 114>
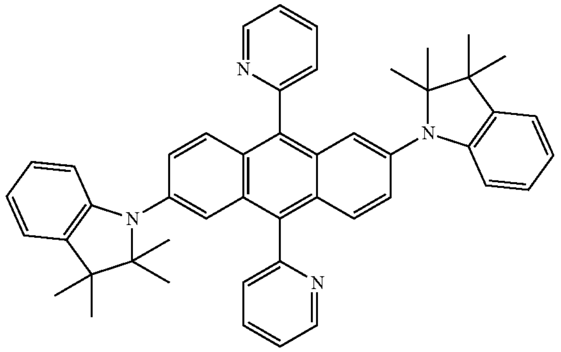
<Compound 115>
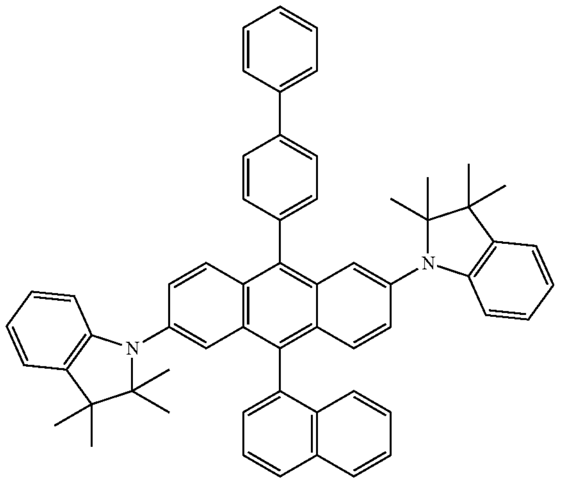
<Compound 116>
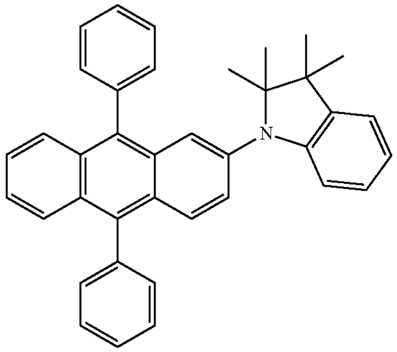
<Compound 117>
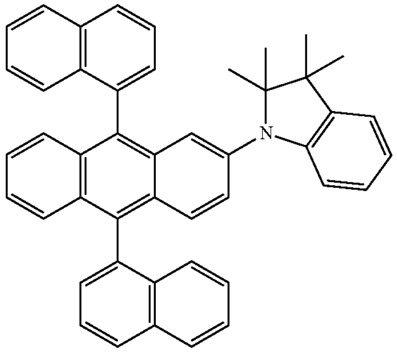
-continued
<Compound 118>
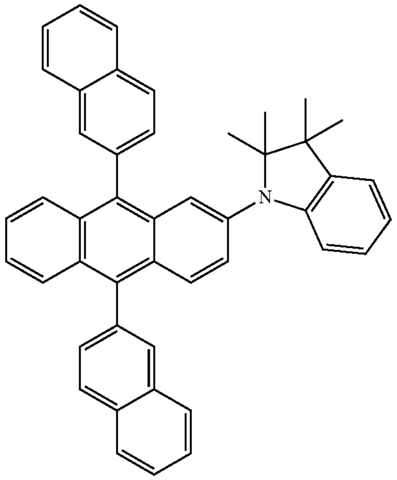
<Compound 119>
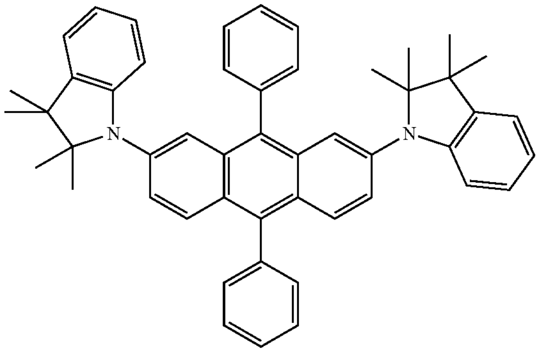
<Compound 120>
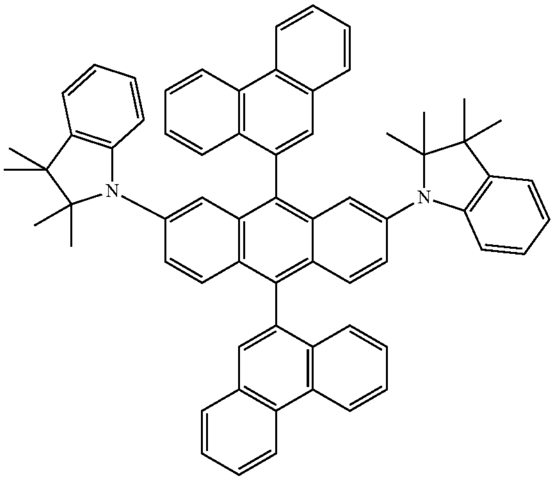

-continued
<Compound 121>
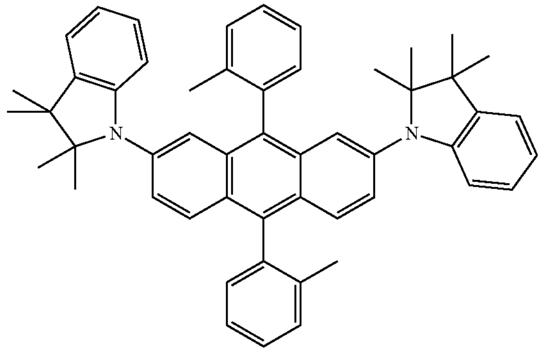
<Compound 122>
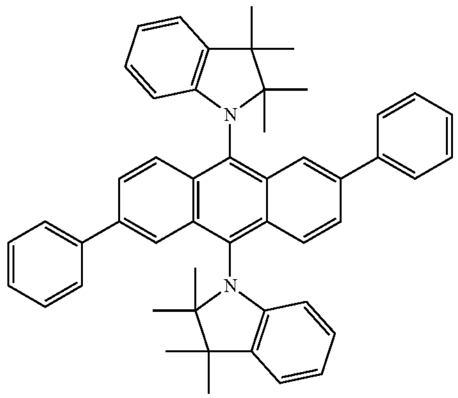
<Compound 123>
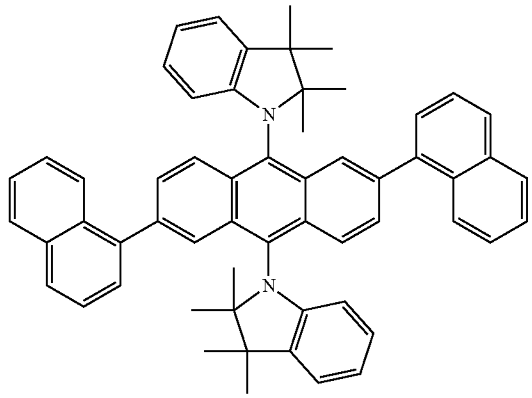
<Compound 124>
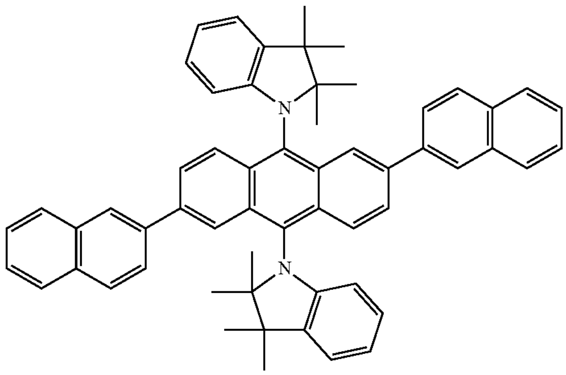
-continued
<Compound 125>
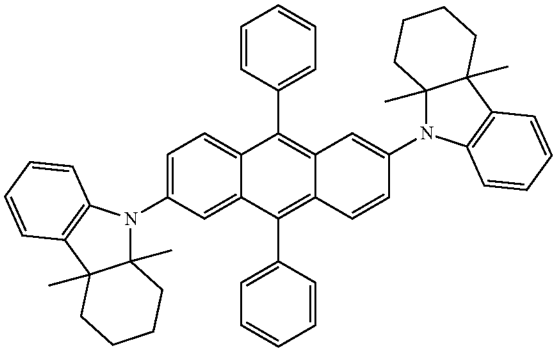
<Compound 126>
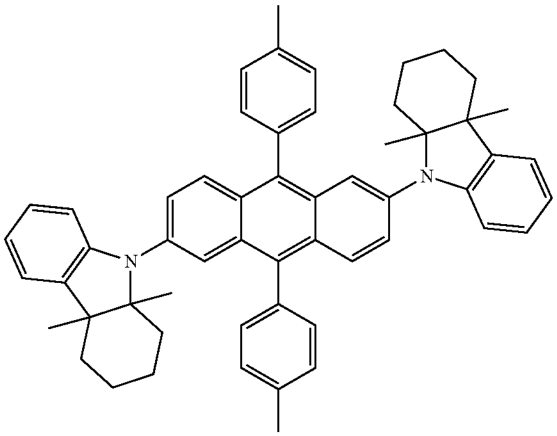
<Compound 127>
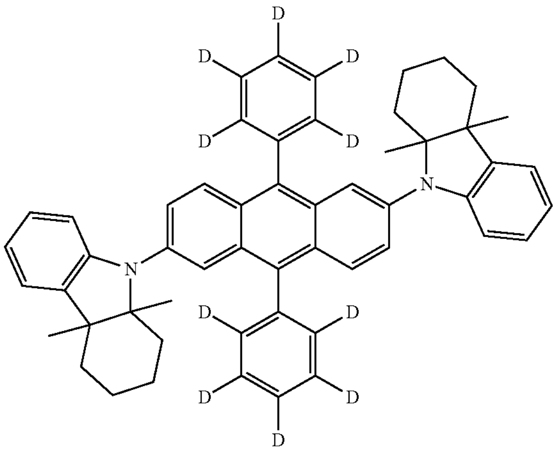

-continued
<Compound 128>
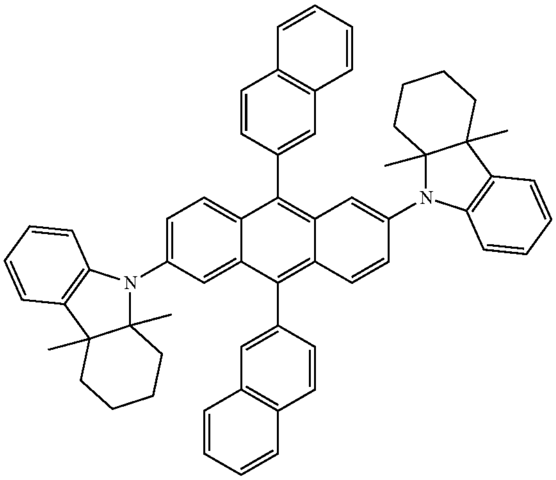
<Compound 129>
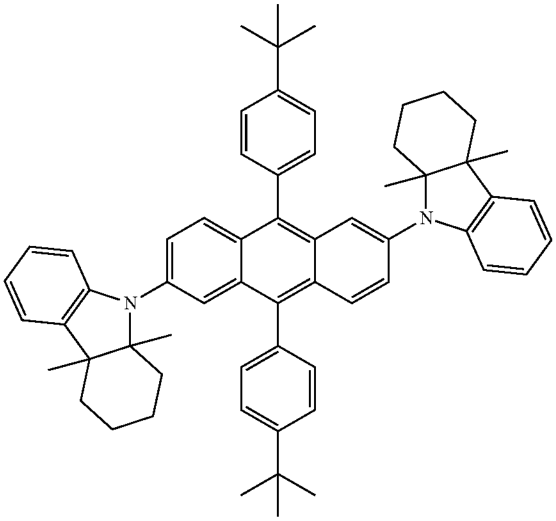
-continued
<Compound 130>
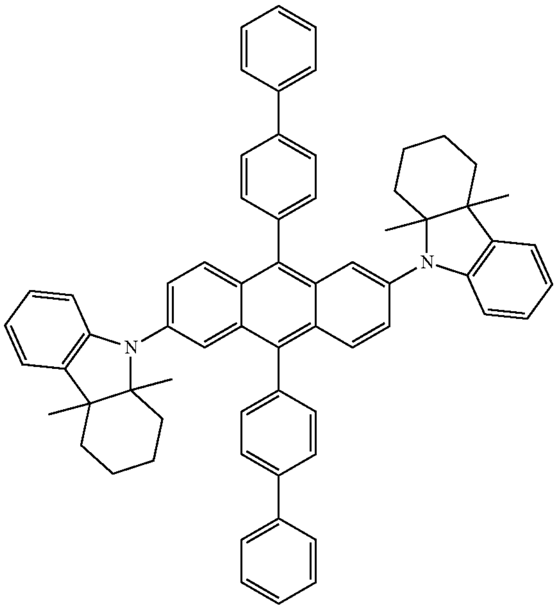
<Compound 131>
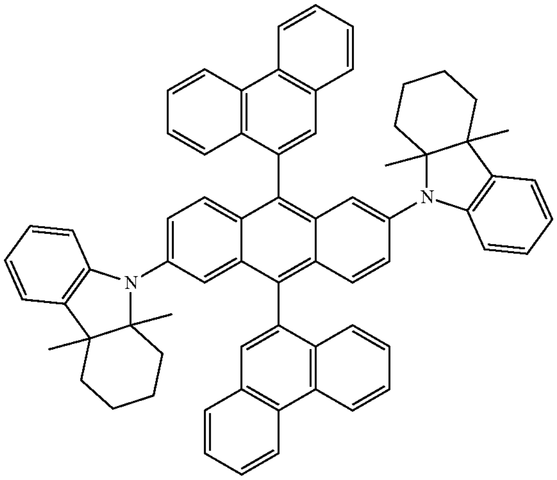
<Compound 132>
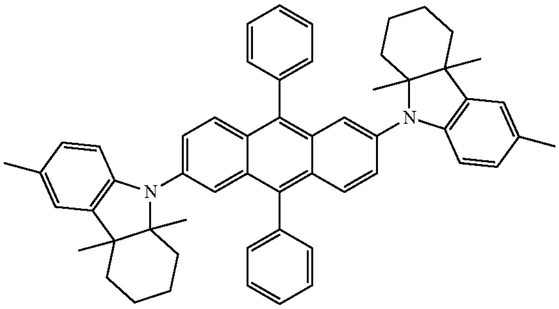

-continued
<Compound 133>
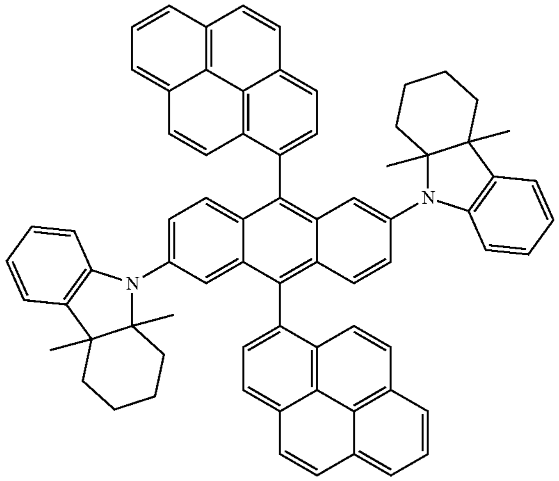
<Compound 134>
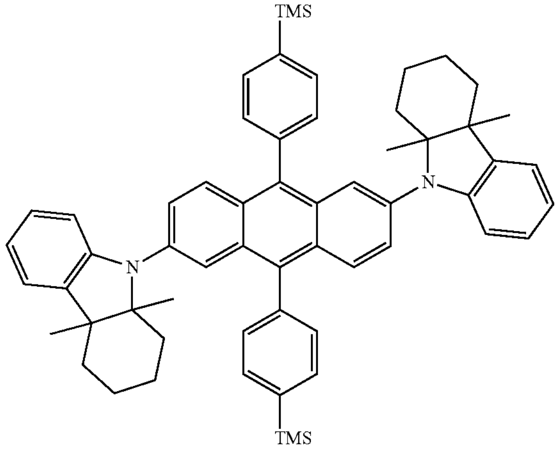
<Compound 135>
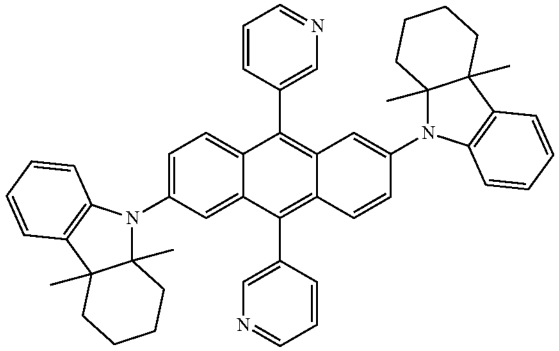
-continued
<Compound 136>
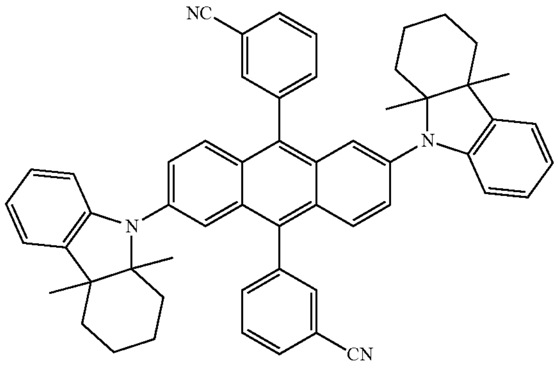
<Compound 137>
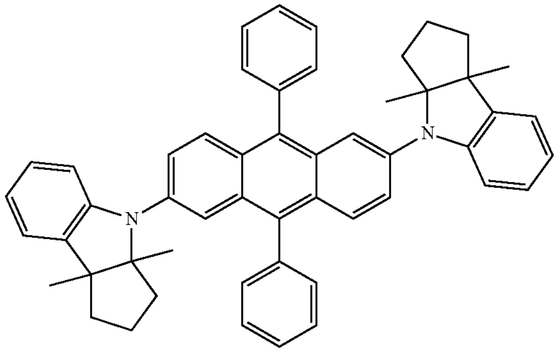
<Compound 138>
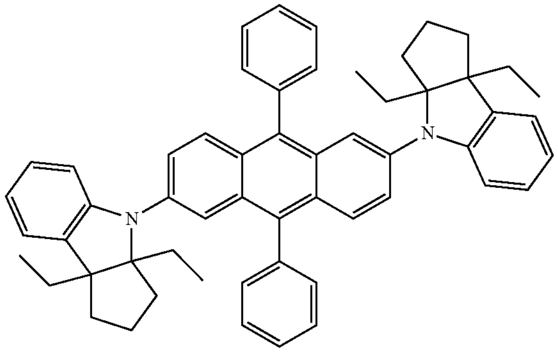
<Compound 139>
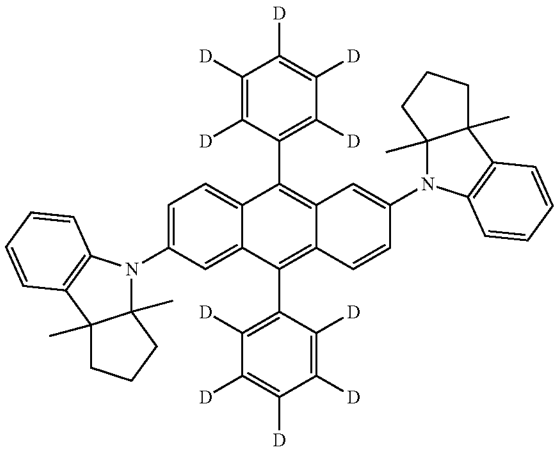

-continued

<Compound 140>

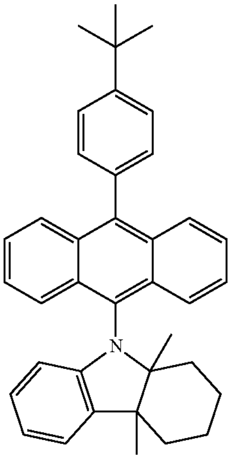

<Compound 141>

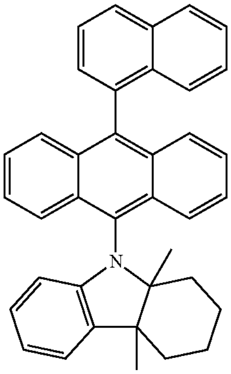

<Compound 142>

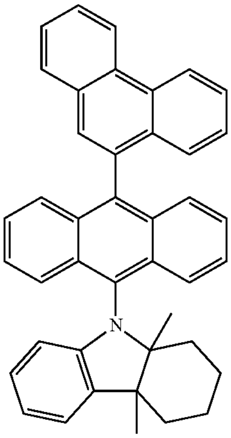

-continued

<Compound 143>

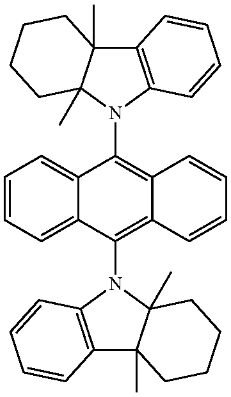

<Compound 144>

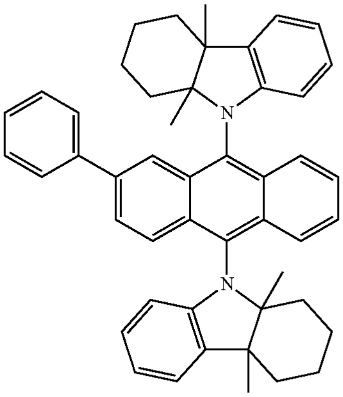

<Compound 145>

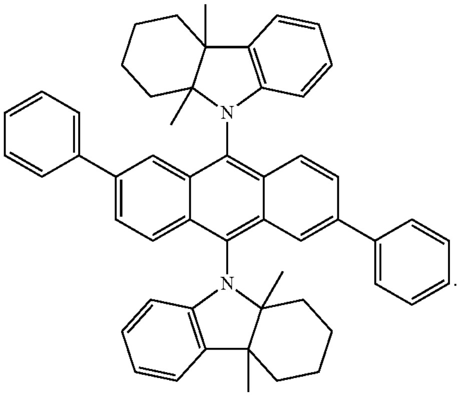

Meanwhile, the compounds represented by Chemical Formulas B and C to H-4, which are available for the charge balance control layer, are technically characterized in that a linker L is bonded to the compounds at position 9 of the anthracene moiety and is connected to a dibenzofuran ring at position 1 or 2 of the dibenzofuran moiety.

[Diagram 1]

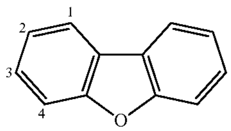

In Chemical Formulas B and C, the linker L may be a single bond or one selected from among the following Structural Formulas 1 and 2:

[Structural Formula 1]

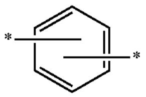

[Structural Formula 2]

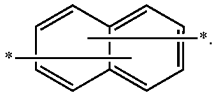

In the linkers, each of the unsubstituted carbon atoms of the aromatic ring moiety is bound with a hydrogen atom or a deuterium atom.

In addition, the substituents Ar1 and Ar2 in Chemical Formulas B and C may each be a substituted or unsubstituted aryl of 6 to 18 carbon atoms.

Concrete examples of the compounds represented by Chemical Formula A or B in the present disclosure include, but are not limited to, the compounds represented by the following Chemical Formulas 1 to 75:

<Compound 1>

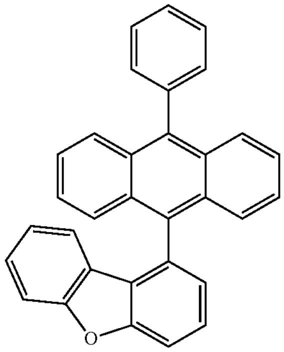

<Compound 2>

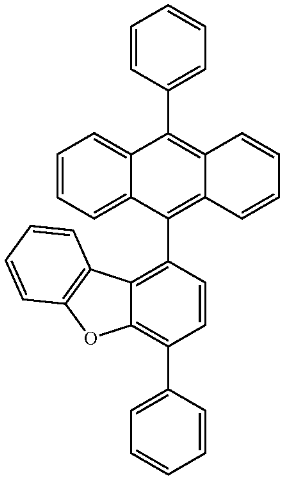

-continued

<Compound 3>

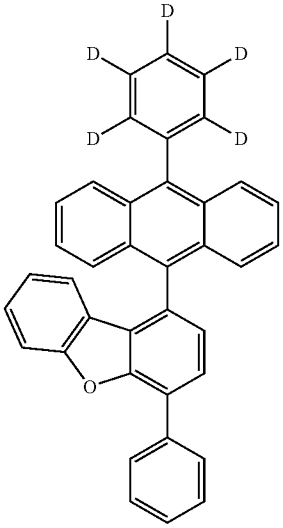

<Compound 4>

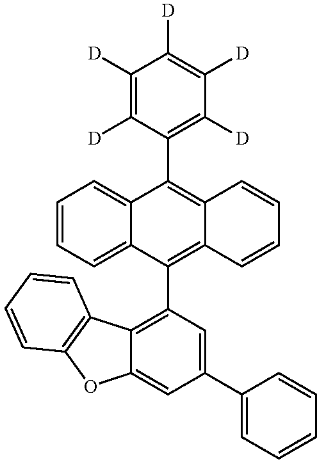

<Compound 5>

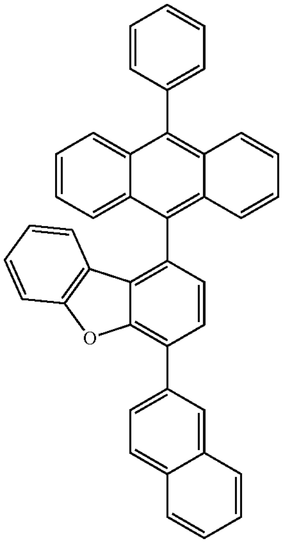

-continued
<Compound 6>
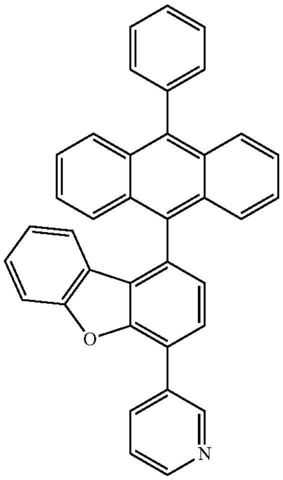
<Compound 7>
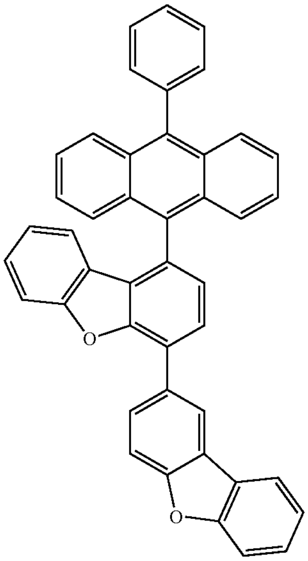
<Compound 8>
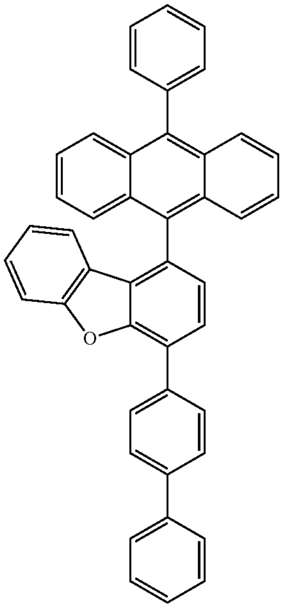
-continued
<Compound 9>
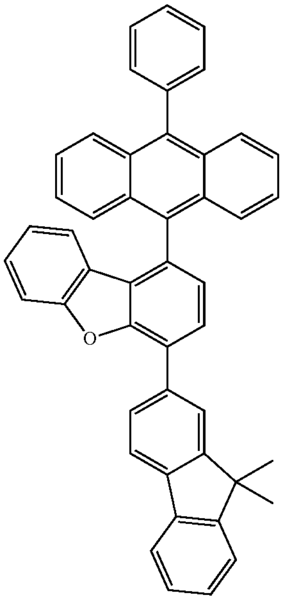
<Compound 10>
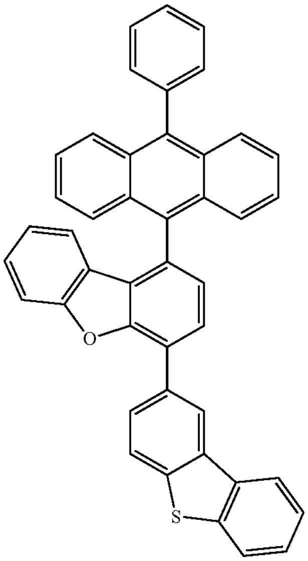

-continued
<Compound 11>
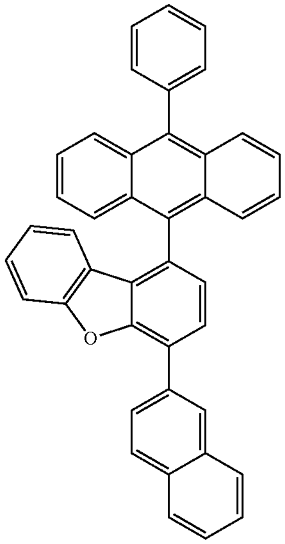
<Compound 12>
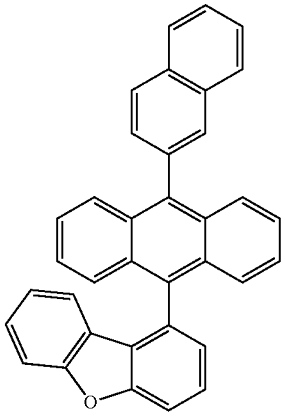
<Compound 13>
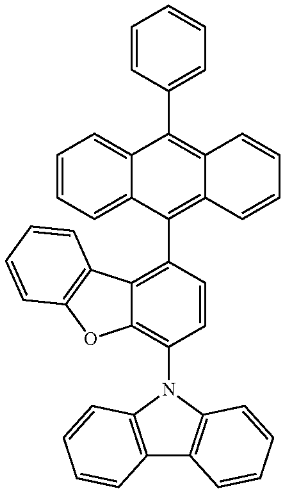
-continued
<Compound 14>
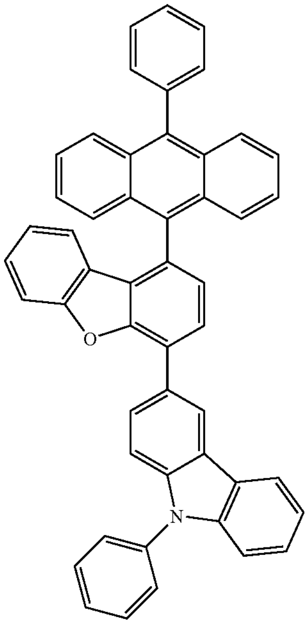
<Compound 15>
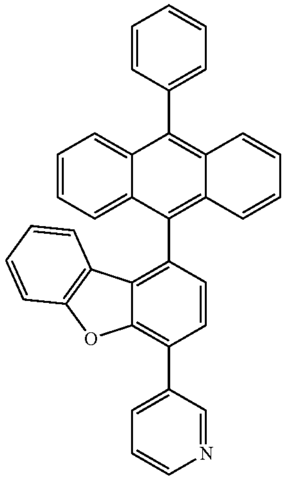
<Compound 16>
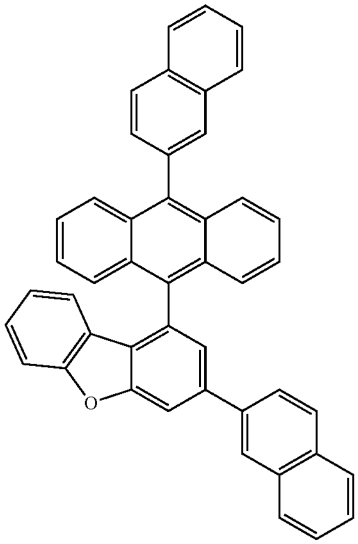

-continued
<Compound 17>
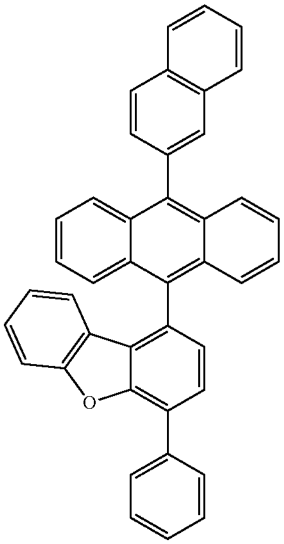
<Compound 18>
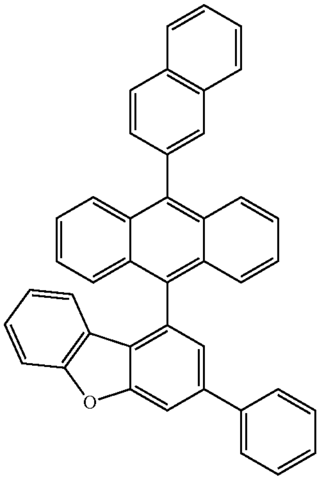
<Compound 19>
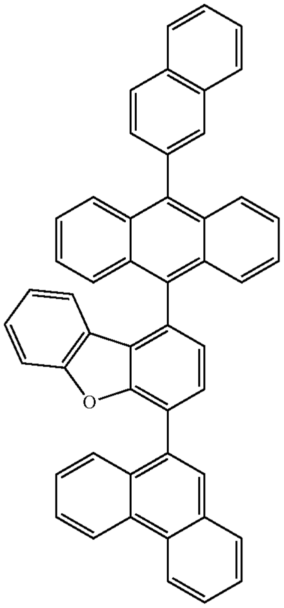
-continued
<Compound 20>
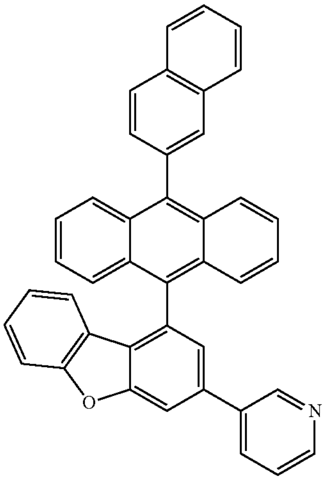
<Compound 21>
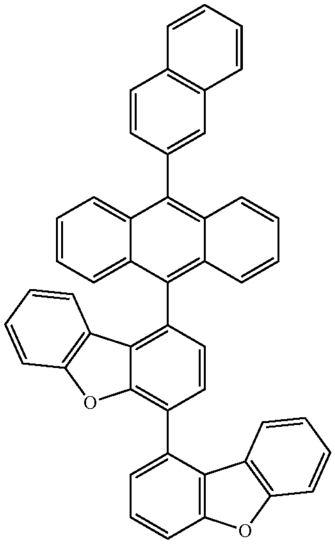
<Compound 22>
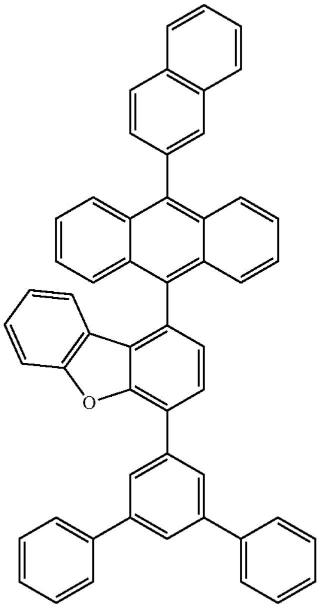

-continued
<Compound 23>
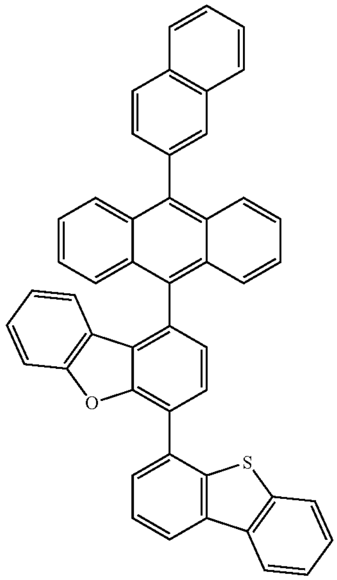
<Compound 24>
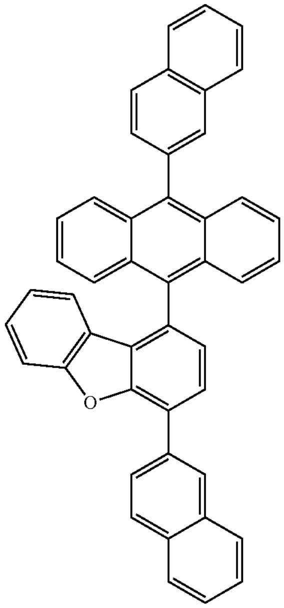
-continued
<Compound 25>
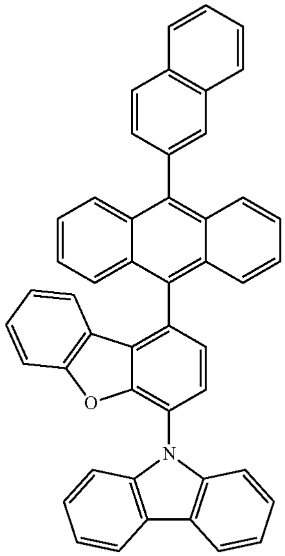
<Compound 26>
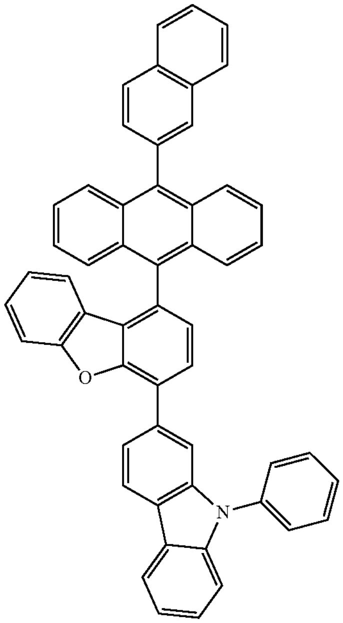

-continued
<Compound 27>
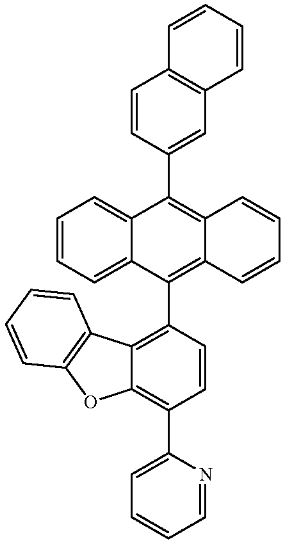
<Compound 28>
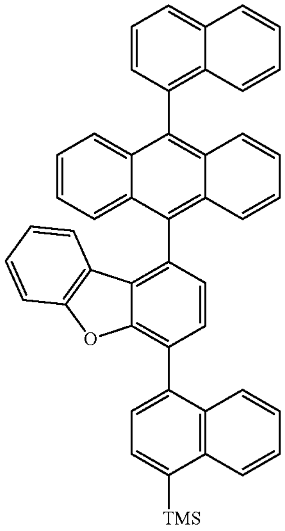
<Compound 29>
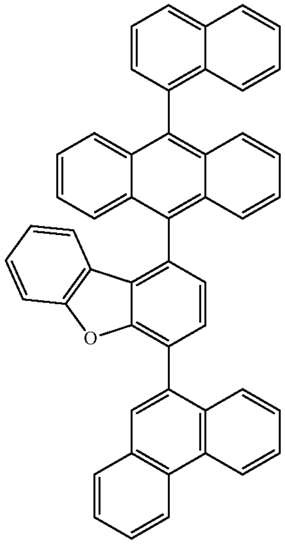
-continued
<Compound 30>
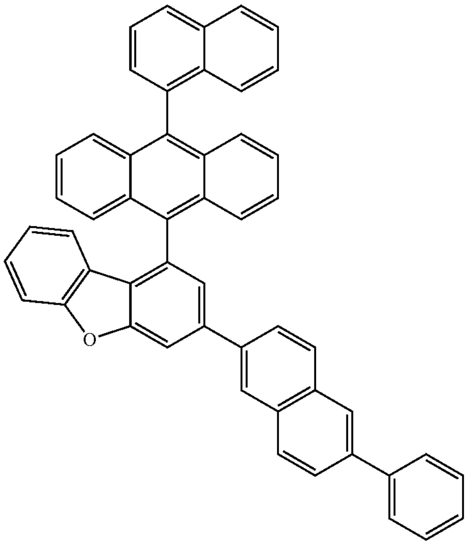
<Compound 31>
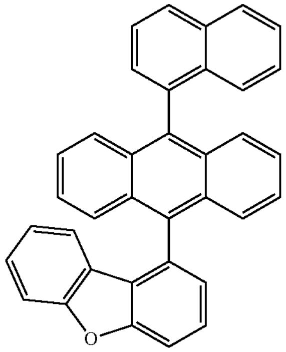
<Compound 32>
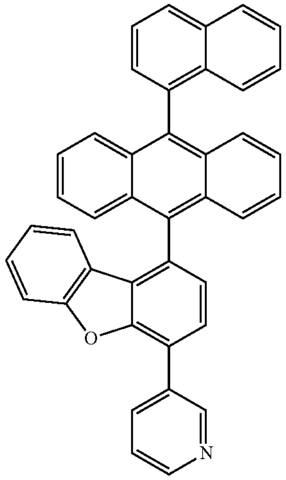

-continued
<Compound 33>
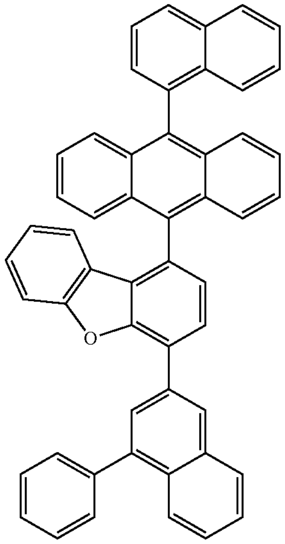
<Compound 34>
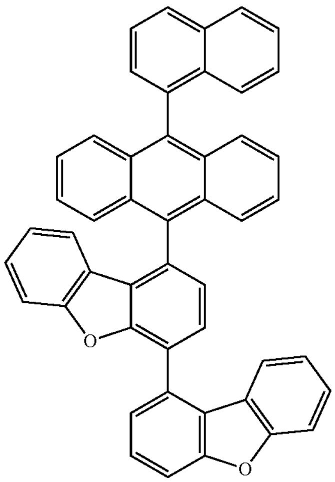
<Compound 35>
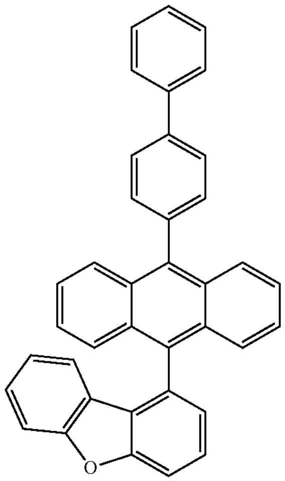
-continued
<Compound 36>
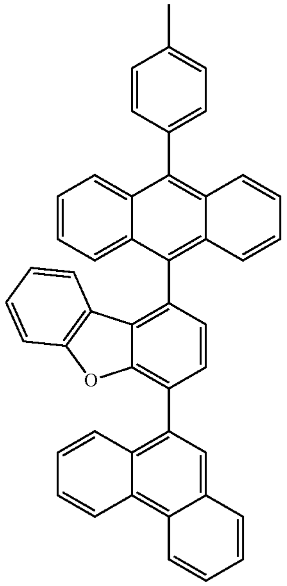
<Compound 37>
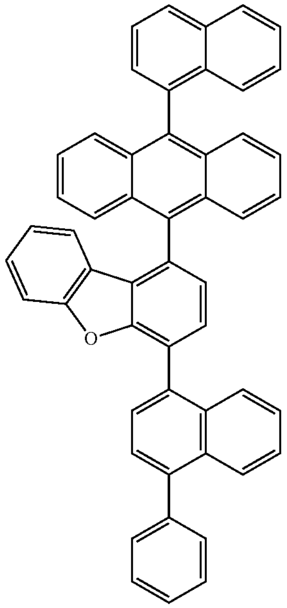

-continued
<Compound 38>
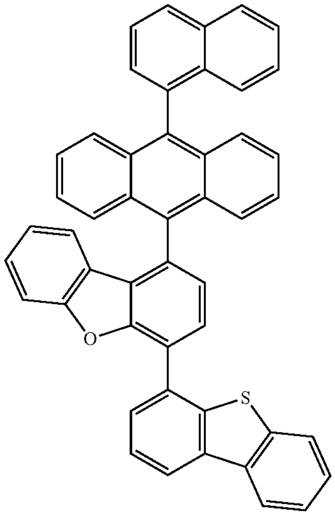
<Compound 39>
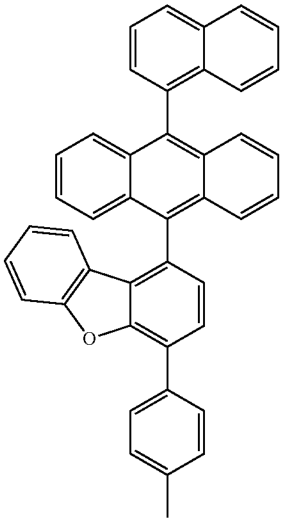
<Compound 40>
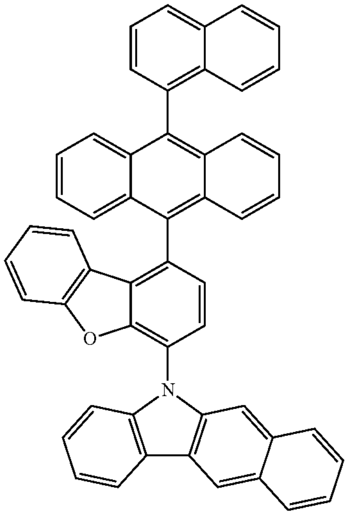
-continued
<Compound 41>
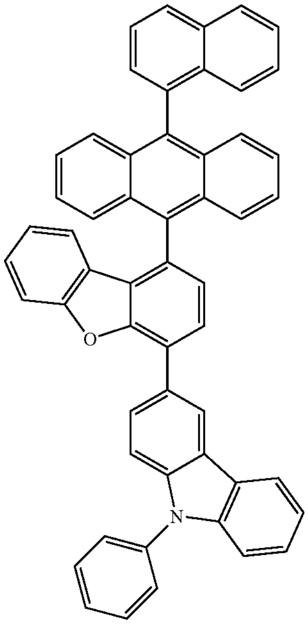
<Compound 42>
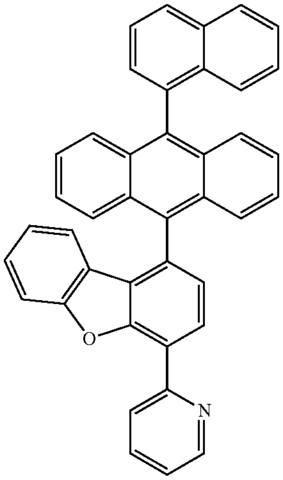

-continued
<Compound 43>
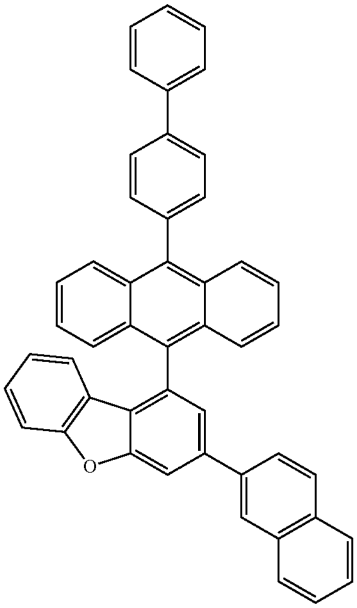
<Compound 44>
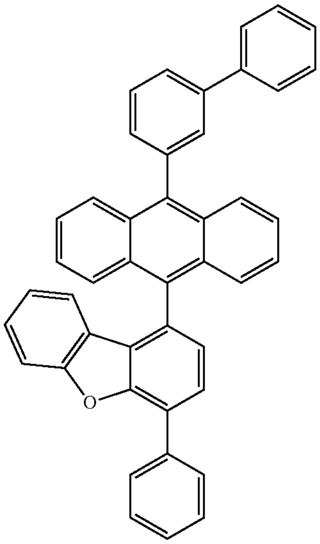
<Compound 45>
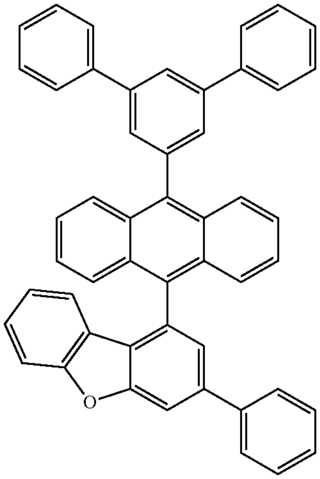
-continued
<Compound 46>
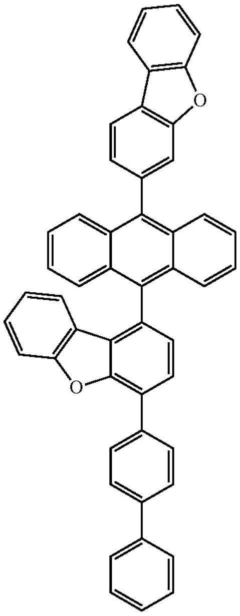
<Compound 47>
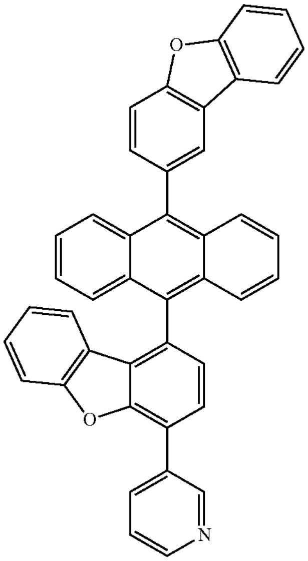

-continued
<Compound 48>
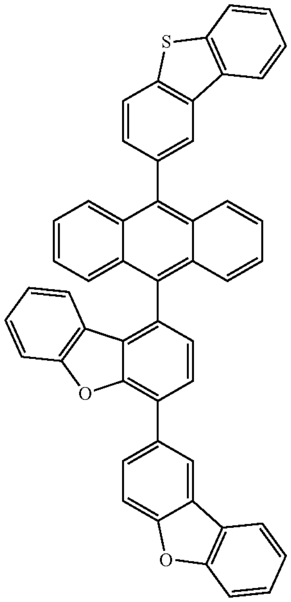
<Compound 49>
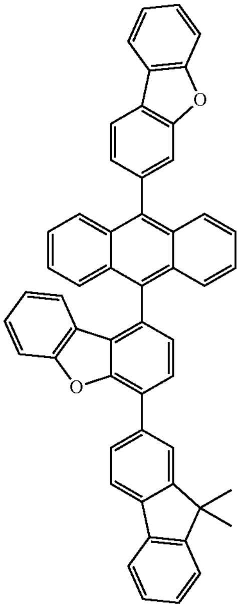
-continued
<Compound 50>
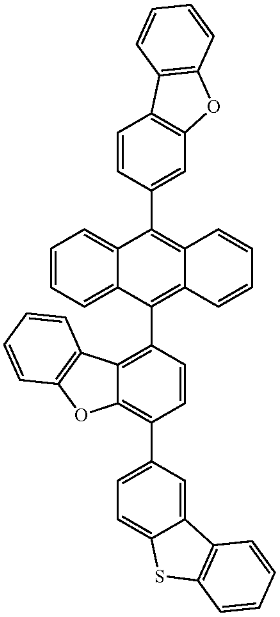
<Compound 51>
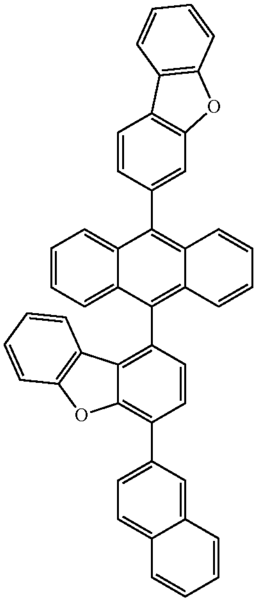

-continued
<Compound 52>
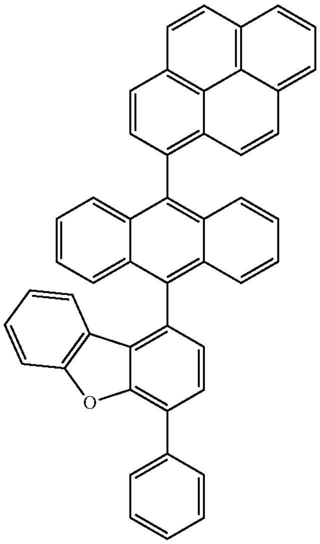
<Compound 53>
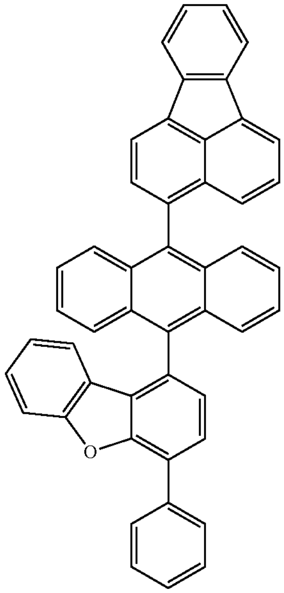
<Compound 54>
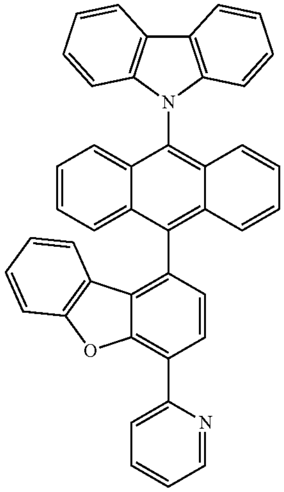
-continued
<Compound 55>
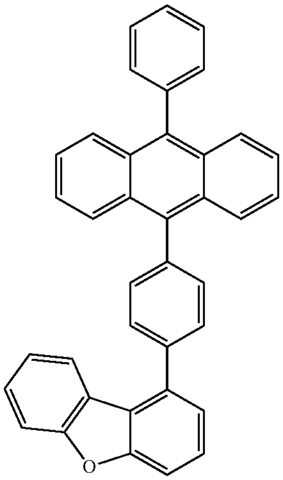
<Compound 56>
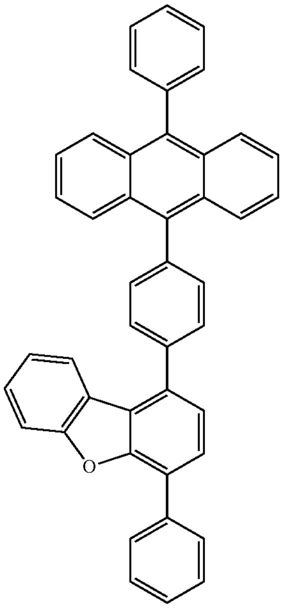

-continued
<Compound 57>
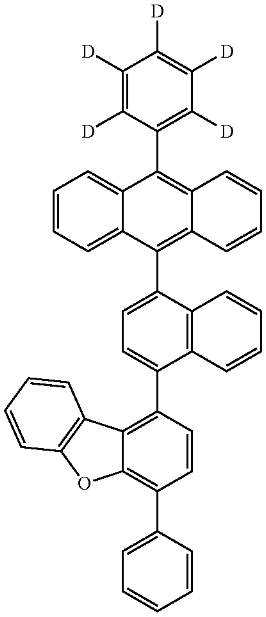
<Compound 58>
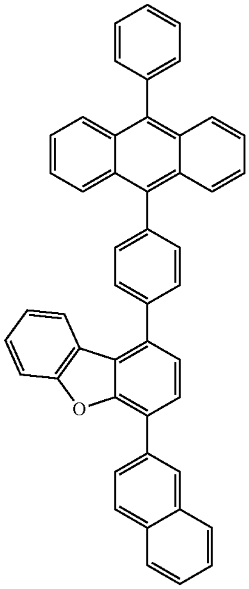
-continued
<Compound 59>
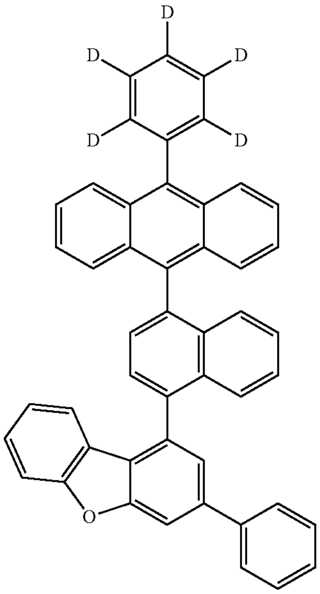
<Compound 60>
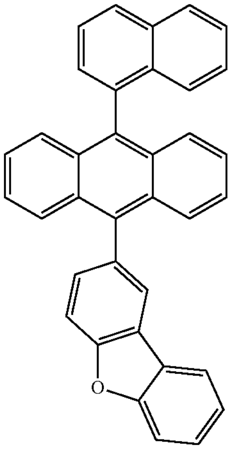
<Compound 61>
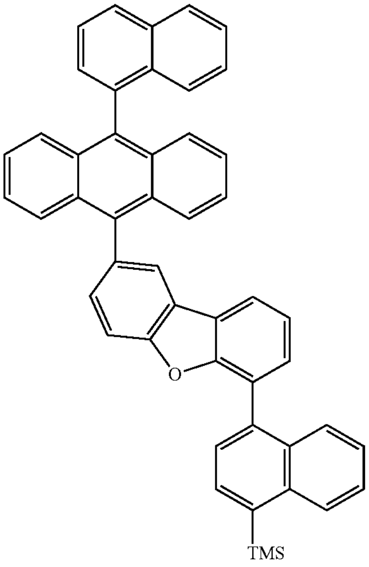

-continued
<Compound 62>
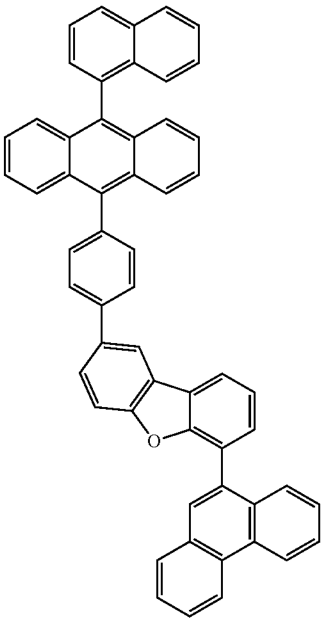
<Compound 63>
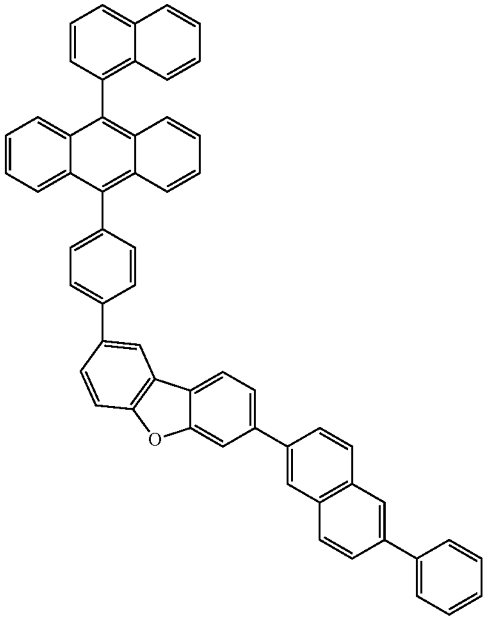
-continued
<Compound 64>
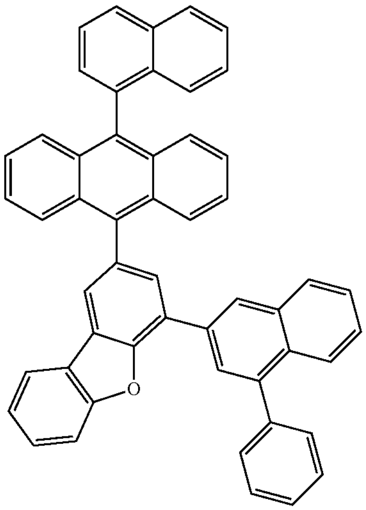
<Compound 65>
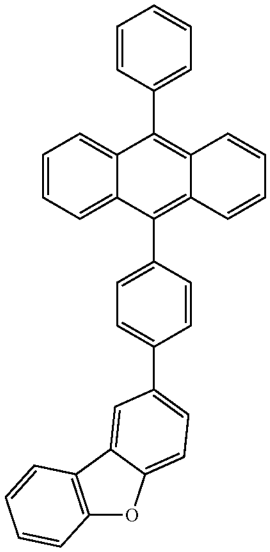
<Compound 66>
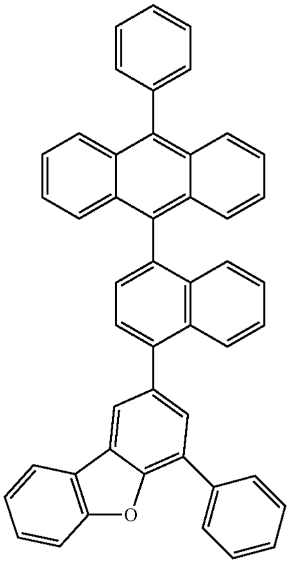

-continued
<Compound 67>
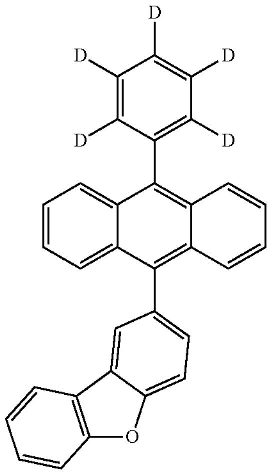
<Compound 68>
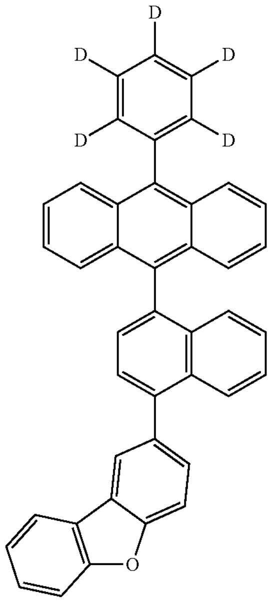
<Compound 69>
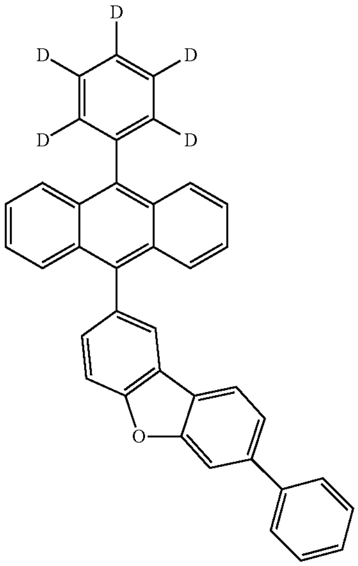
-continued
<Compound 70>
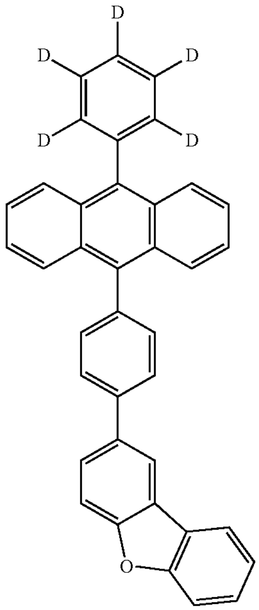
<Compound 71>
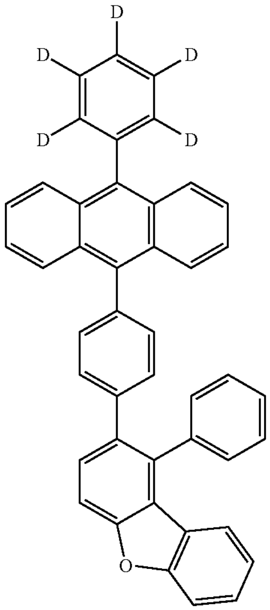

-continued

<Compound 72>

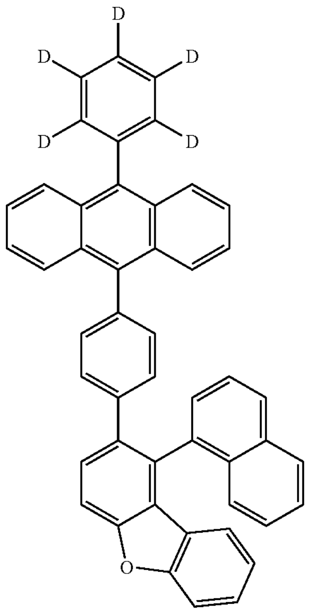

<Compound 73>

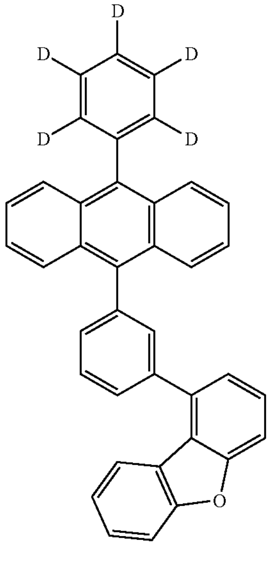

-continued

<Compound 74>

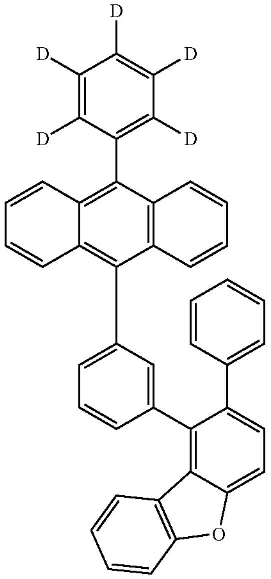

<Compound 75>

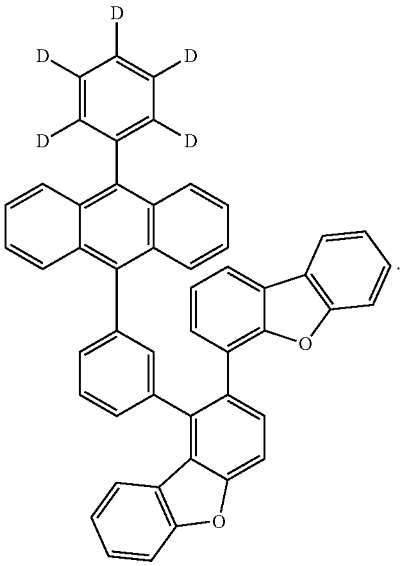

Below, the organic light-emitting diode according to an embodiment of the present disclosure is explained with reference to FIG. 1.

FIG. 1 is a schematic cross-sectional view of the structure of an organic light-emitting diode according to some embodiments of the present disclosure.

As shown in FIG. 1, the organic light-emitting diode comprises an anode 20, a hole transport layer 40, an organic light-emitting layer 50 including a host and a dopant, a charge balance control layer 55, an electron transport layer 60, and a cathode 80, sequentially, which corresponds to an organic light-emitting diode in which an anode and a cathode serve as a first and a second electrode, respectively, and a hole transport layer disposed between the anode and a light-emitting layer and an electron transport layer is disposed between a charge balance control layer and the cathode.

That is, a charge balance control layer 55 including at least one of the compounds represented by Chemical Formula B or C is disposed between the light-emitting layer 50 and the electron transport layer 60, and the light-emitting layer includes at least one of the compounds represented by Chemical Formula A as a dopant.

In addition, the organic light-emitting diode according to an embodiment of the present disclosure may comprise a hole injection layer 30 between the anode 20 and the hole transport layer 40, and an electron injection layer 70 between the electron transport layer 60 and the cathode 80.

Reference is made to FIG. 1 with regard to the organic light-emitting device of the present disclosure and the fabrication thereof.

First, a substrate 10 is coated with an anode electrode material to form an anode 20 thereon. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO), which are transparent and superior in terms of conductivity, may be used. A hole injection layer material is applied on the anode electrode 20 by thermal deposition in a vacuum or by spin coating to form a hole injection layer 30. Subsequently, thermal deposition in a vacuum or by spin coating may also be conducted to form a hole transport layer 40 with a hole transport layer material on the hole injection layer 30.

No particular limitations are imposed on the hole injection layer material, as long as it is one that is typically used in the art. For example, mention may be made of 2-TNATA [4,4',4"-tris(2-naphthylphenyl-phenylamino)-triphenylamine], NPD [N,N'-di(1-naphthyl)-N,N'-diphenylbenzidine)], TPD [N,N'-diphenyl-N,N'-bis(3-methylphenyl)-1,1'-biphenyl-4,4'-diamine], and DNTPD [N,N'-diphenyl-N,N'-bis-[4-(phenyl-m-tolyl-amino)-phenyl]-biphenyl-4,4'-diamine], but is not limited thereto.

Any material that is typically used in the art may be selected for the hole transport layer without particular limitation. Examples include, but are not limited to, N,N'-bis(3-methylphenyl)-N,N'-diphenyl-[1,1-biphenyl]-4,4'-diamine (TPD) and N,N'-di(naphthalen-1-yl)-N,N'-diphenylbenzidine (a-NPD).

Then, an organic light-emitting layer 50 is deposited on the hole transport layer 40 by vacuum deposition or spin coating, followed by the formation of a charge balance control layer 55 according to the present disclosure on the organic light-emitting layer 50 by deposition in a vacuum or by spin coating.

Here, the light-emitting layer may be composed of a host and a dopant the materials of which are as described above.

In some embodiments of the present disclosure, the light-emitting layer particularly ranges in thickness from 50 to 2,000 Å.

In the light-emitting layer according to the present disclosure, a dopant material may be used in combination with a host material. When the light-emitting layer includes a host and a dopant, the content of the dopant in the light-emitting layer may range from about 0.01 to 20 parts by weight based on 100 parts by weight of the host, but is not limited thereto.

The host used in the present disclosure may be an anthracene compound, but is not limited thereto.

When used as the host in the present disclosure, the anthracene compound may be represented by the following Chemical Formula D:

[Chemical Formula D]

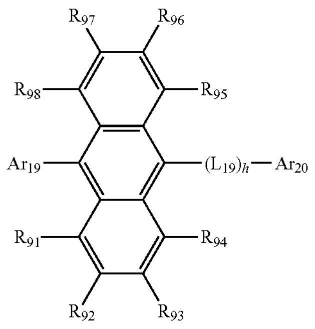

wherein $R_{91}$ to $R_{98}$ may be the same or different and are as defined for substituents $R_1$ to $R_{10}$ in Chemical Formula A, $Ar_{19}$ and $Ar_{20}$ may be the same or different and are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, and a substituted or unsubstituted arylsilyl of 6 to 30 carbon atoms;

$L_{19}$ is a single bond or any one selected from among a substituted or unsubstituted arylene of 6 to 20 carbon atoms and a substituted or unsubstituted heteroarylene of 2 to 20 carbon atoms, h is an integer of 1 to 3, with a proviso that when h is 2 or greater, the corresponding $L_{19}$'s are may be the same or different.

In greater detail, $Ar_{19}$ in the anthracene derivative represented by the following Chemical Formula D may be a substituent represented by the following Chemical Formula D-1:

[Chemical Formula D-1]

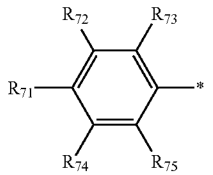

wherein $R_{71}$ to $R_{75}$ may be the same or different and are each as defined for the substituents $R_1$ to $R_{10}$ in Chemical Formula A, with a proviso that adjacent substituents may form a saturated or unsaturated ring.

In this case, $L_{19}$ in the anthracene derivative of Chemical Formula D may be a single bond or a substituted or unsubstituted arylene of 6 to 20 carbon atoms, and h may be 1 or 2, with the proviso that when h is 2, corresponding $L_{19}$'s may be the same or different.

In addition to the above-mentioned dopants and hosts, the light-emitting layer may further include various host and dopant materials.

Following the formation of the charge balance control layer 55 according to the present disclosure on the light-emitting layer, an electron transport layer 60 may be deposited using a vacuum deposition method or a spin coating method and then overlaid with an electron injection layer 70. A cathode metal is deposited on the electron injection layer 70 by thermal deposition in a vacuum to form a cathode 80, thus obtaining an organic light-emitting diode (OLED).

So long as it functions to stably transport the electrons from a cathode, any known material may be used for the electron transport layer. Examples of the known electron transport material include quinoline derivatives, particularly tris(8-quinolinolate)aluminum ($Alq_3$), Liq, TAZ, BAlq, beryllium bis(benzoquinolin-10-olate ($Bebq_2$), compound 201, compound 202, BCP, and the oxadiazole derivatives PBD, BMD, and BND, but are not limited thereto.

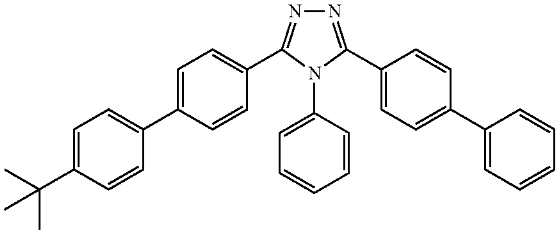

TAZ

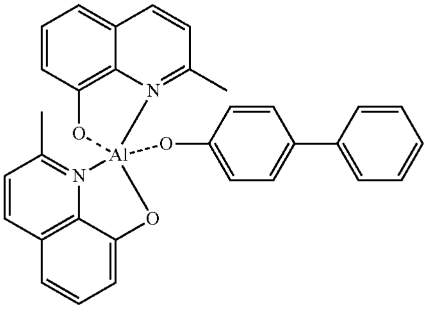

Balq 27

-continued

<Compound 201>

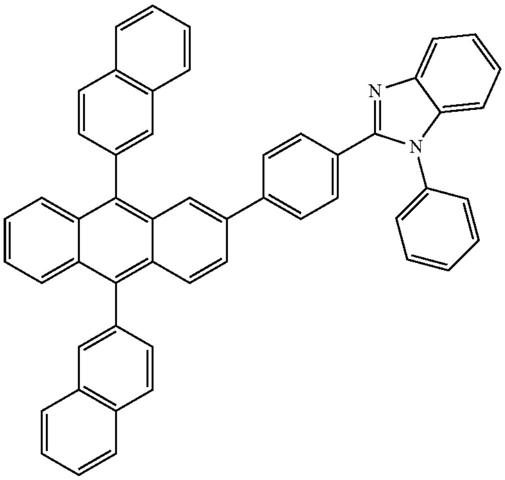

<Compound 202>

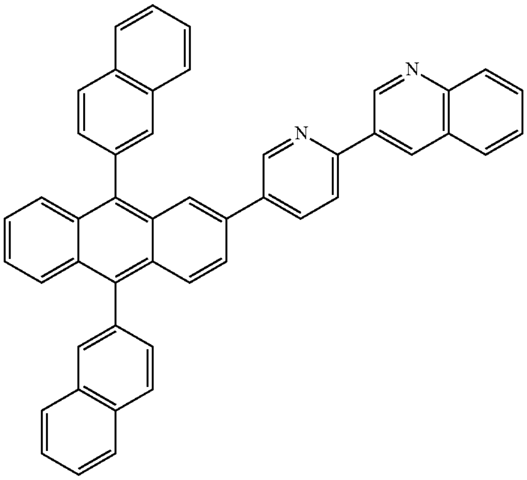

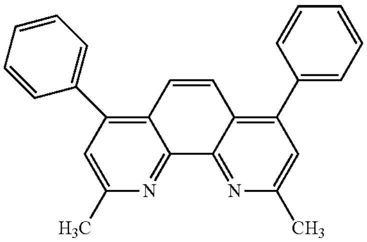

BCP

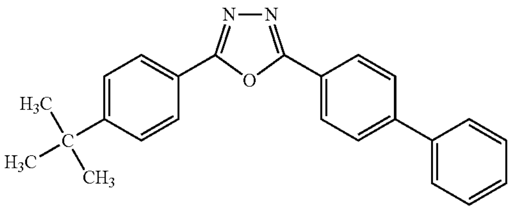

PBD

-continued

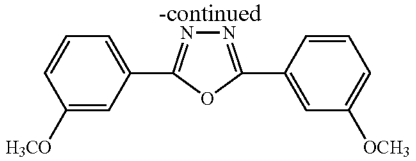

BMD

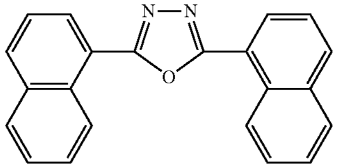

BND

An electron injection layer (EIL) that is adapted to facilitate the injection of electrons from the cathode may be positioned on the electron transport layer in the organic light-emitting diode of the present disclosure. Any known material may be available for forming the electron injection layer, without particular limitations, as long as it is usually used in the art.

By way of example, the material for the electron injection layer may be CsF, NaF, LiF, NaCl, $Li_2O$, or BaO. The conditions for depositing the electron injection layer are dependent on the compound that is employed, but may fall within the range of conditions for the formation of the hole injection layer.

The electron injection layer may range in thickness from about 1 Å to about 100 Å, and particularly from about 3 Å to about 90 Å. Given this thickness range, the electron injection layer can exhibit satisfactory electron injection properties without an actual increase in driving voltage.

The cathode may be made of a metal or metal alloy such as lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be employed to form a transparent cathode for a top-emitting organic light-emitting diode.

In another embodiment, the light-emitting diode of the present disclosure may further comprise a light-emitting layer, made of a blue light-emitting material, a green light-emitting material, or a red light-emitting material, which can emit light in a wavelength range of 380 nm to 800 nm. That is, the light-emitting layer in the organic light-emitting diode of the present disclosure may have a multilayer structure in which the additional blue, green, and/or red light-emitting layer may be made of a fluorescent or phosphorescent material.

In accordance with some embodiments of the present disclosure, the affinity $A_{cb}$ (eV) of the charge balance control layer may fall between the affinity $A_h$ (eV) of the host in the light-emitting layer and the affinity $A_e$ (eV) of the electron transport layer ($A_h \geq A_{cb} \geq A_e$).

Figure 2:
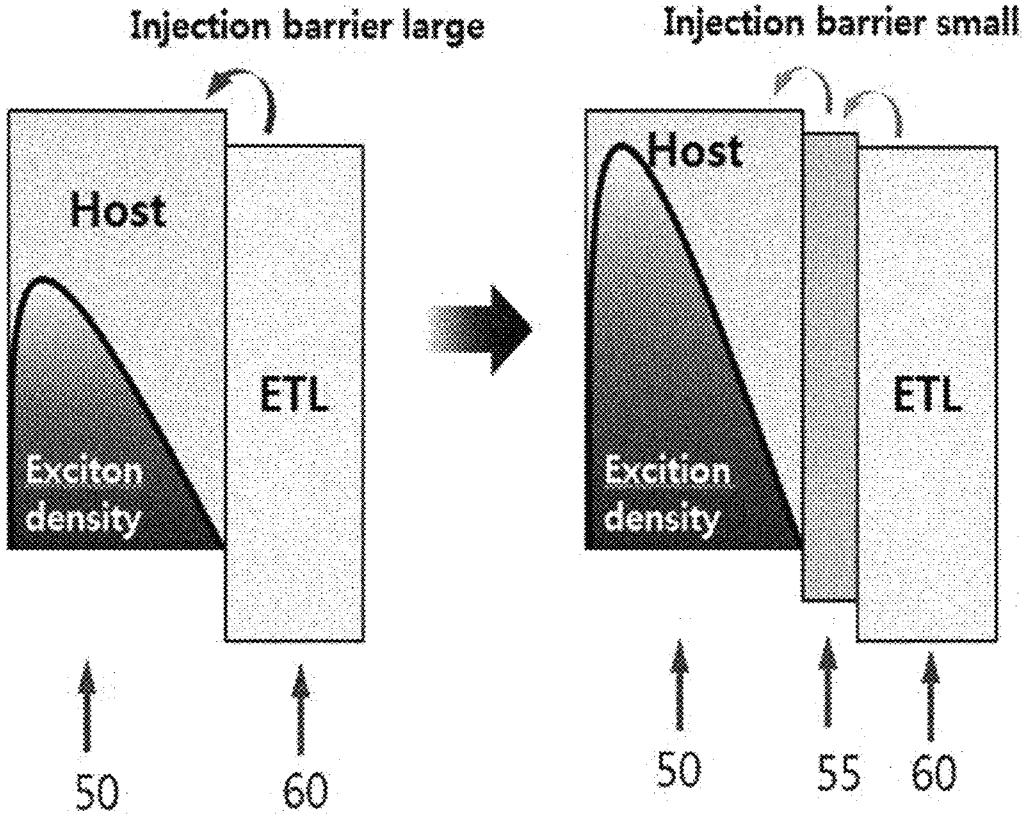
FIG. 2 is a schematic diagram of the structures of organic light-emitting devices in which a charge balance control layer is present and absent, respectively.
Figure 3:
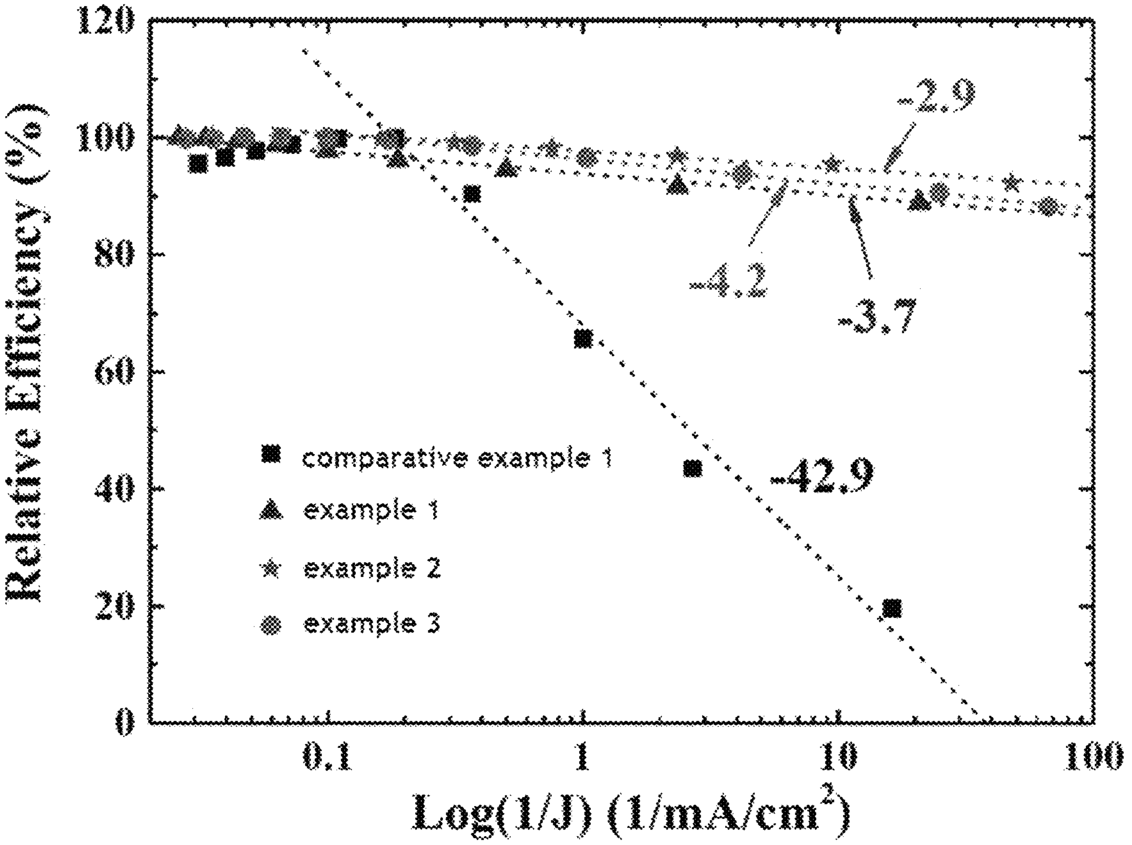
FIG. 3 is a plot of luminance reduction rates in low dynamic ranges of an organic light-emitting diode according to one embodiment of the present disclosure.
Figure 4:
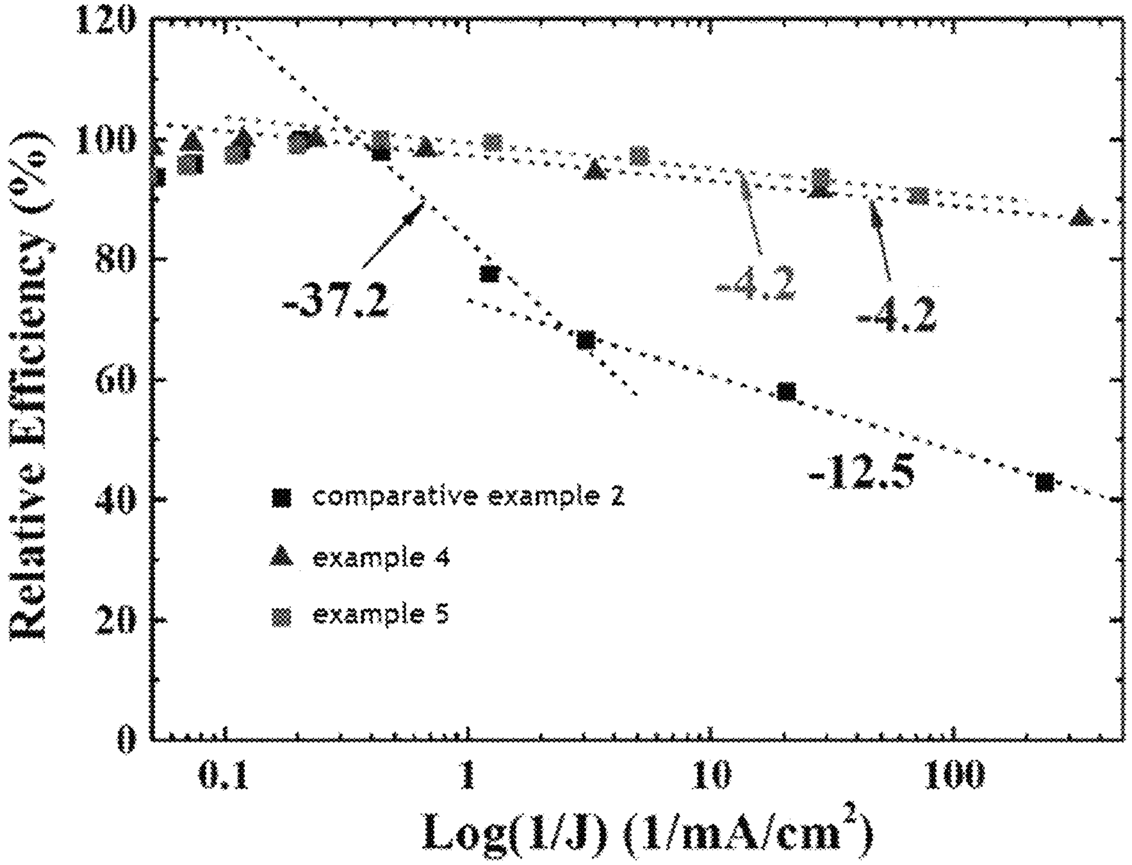
FIG. 4 is a plot of luminance reduction rates in low dynamic ranges of an organic light-emitting diode according to another embodiment of the present disclosure.
Figure 5:
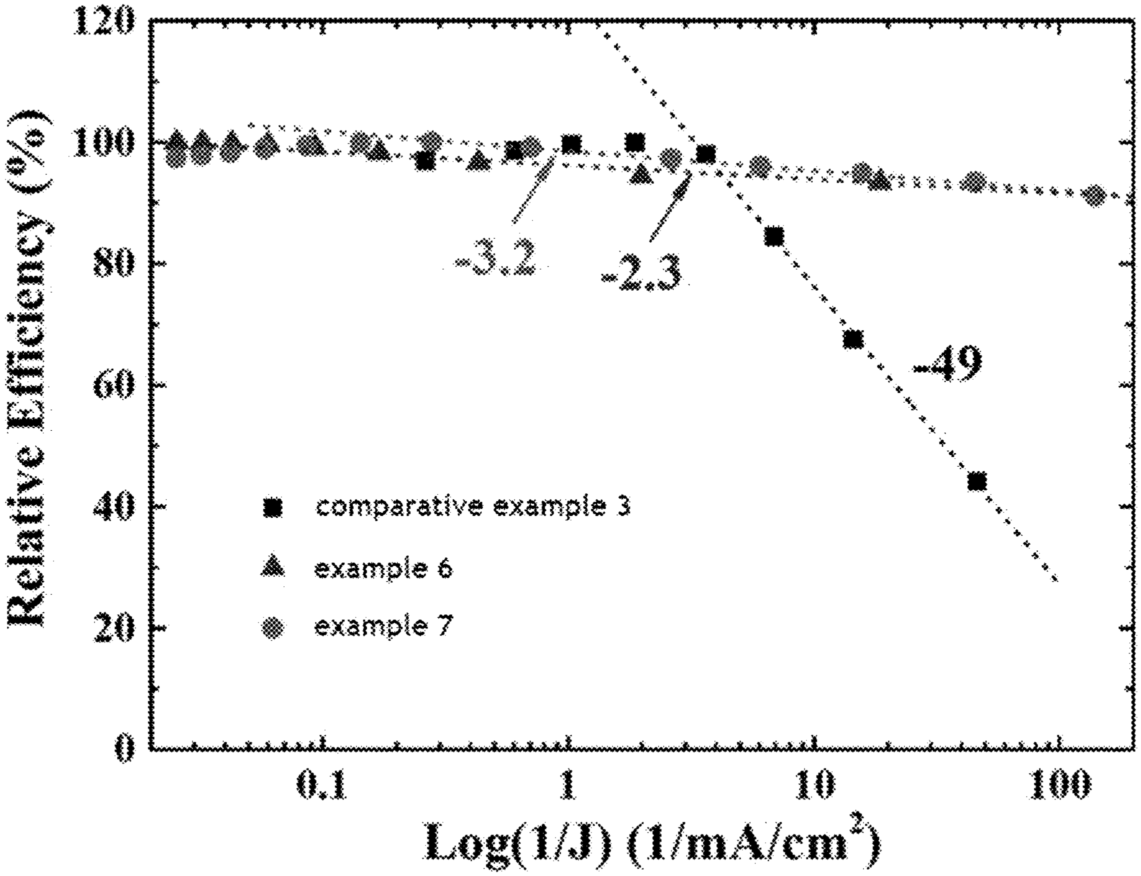
FIG. 5 is a plot of luminance reduction rates in low dynamic ranges of an organic light-emitting diode according to a further embodiment of the present disclosure.
Figure 6:
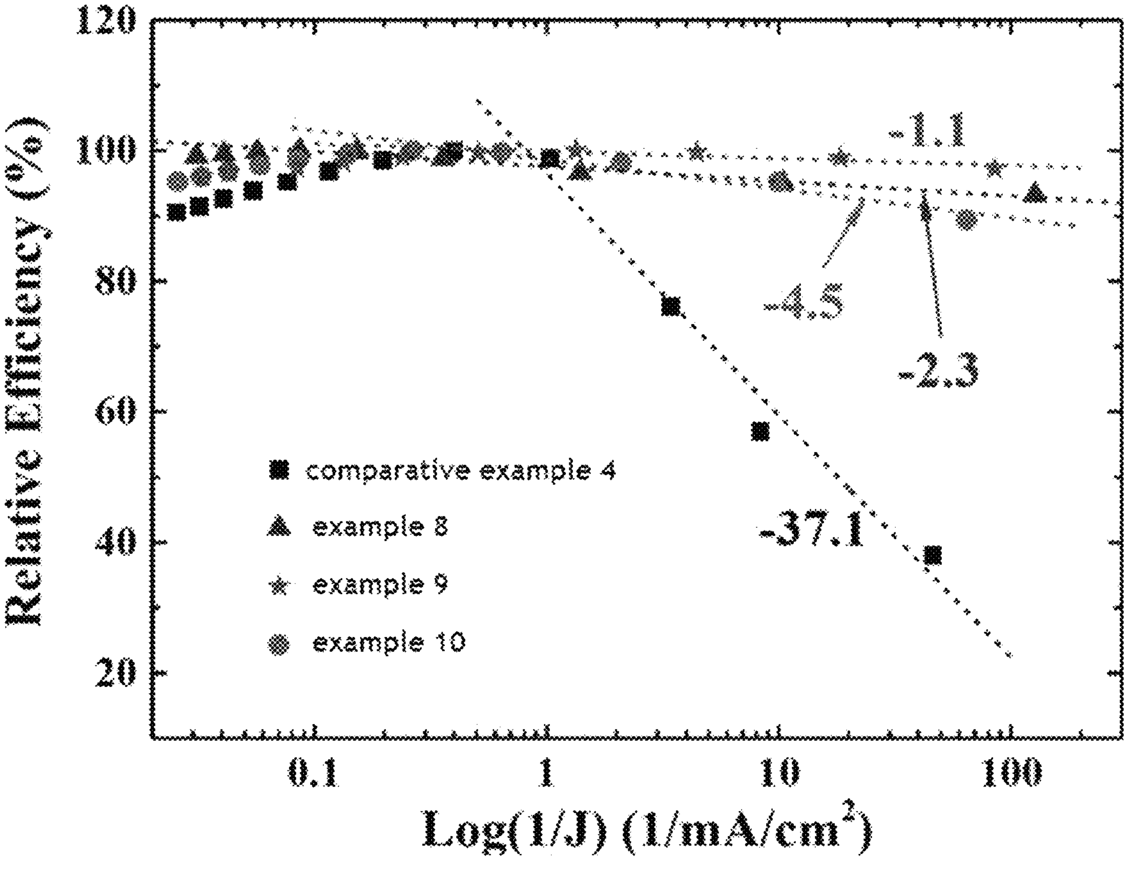
FIG. 6 is a plot of luminance reduction rates in low dynamic ranges of an organic light-emitting diode according to still another embodiment of the present disclosure.

This can be elucidated in greater detail with reference to FIG. 2. FIG. 2 shows the structure of a light-emitting diode in which a charge balance control layer according to an embodiment of the present disclosure is absent (left panel) or present (right panel).

As shown in the left panel of FIG. 2, when the electron transport layer 60 is in direct contact with the light-emitting layer 50, the electrons injected from the cathode are less prone to move through the electron transport layer 60 to the host 50 in the light-emitting layer because there is a large electron injection barrier between the cathode and the host 50, resulting in low exciton density in the host of the light-emitting layer. In contrast, as in the present disclosure, when an affinity $A_{cb}$ (eV) of the charge balance control layer is set to be between an affinity $A_h$ (eV) of the host in the light-emitting layer and an affinity $A_e$ (eV) of the electron transport layer ($A_h \geq A_{cb} \geq A_e$), smaller interlayer electron injection barriers exist, resulting in greater exciton density in the host of the light-emitting layer.

In other words, the charge balance control layer lowers a barrier to electron injection, thus facilitating electron injection into the light-emitting layer.

In addition, the charge balance control layer according to the present disclosure makes an electron injection barrier between the light-emitting layer and the electron transport layer similar to a hole injection barrier attributed to an ionization energy level difference between the light-emitting layer and the hole transport layer, achieving a charge balance between the holes and the electrons and thus alleviating luminance reduction in a low dynamic range of the organic light-emitting diode.

In greater detail, fluorescent materials, such as fluorescent hosts, in organic light-emitting diodes are generally known to have hole mobility greater than electron mobility. In addition to the charge mobility in a light-emitting layer, an electron injection barrier between the light-emitting layer and the electron transport layer and a hole injection barrier attributed to an ionization energy level difference between the light-emitting layer and the hole transport layer fall within the scope of important factors that determine a charge balance and grayscale characteristics in the light-emitting layer of the organic light-emitting. A greater difference between the two barriers requires the application of a higher voltage (higher current) to the diode in order to inject charges into the light-emitting layer.

A great difference between the hole and the electron injection barrier would disrupt a charge balance between two injected species. Given this characteristic, a white OLED suffers from the problem that luminance drastically changes between high and low dynamic ranges with the consequent reduction of color reproducibility in response to driving voltages thereof. In order to solve such a problem, a charge balance control layer is introduced between a light-emitting layer and an electron transport layer in accordance with the present disclosure. The charge balance control layer acts to make a charge balance between holes and electrons in the light-emitting layer, thereby greatly alleviating luminance reduction in a low dynamic range. That is, the introduction of a charge balance control layer advantageously allows electrons and holes to combine in an equilibrium state in a light-emitting layer so that almost none of luminance changes occur in all ranges, whether at high or low voltages.

The configuration of the present disclosure can exhibit more enhanced effects when green luminescent materials having a wavelength of 500 to 580 nm are employed.

According to exemplary embodiments of the present disclosure, the charge balance control layer and the electron transport layer may have an electron mobility of at least $10^{-6}$ $cm^2/Vs$ at an electronic field strength of 0.04 MV/cm to 0.5 MV/cm.

Further, one or more layers selected from among the hole injection layer, the hole transport layer, the light-emitting layer, the charge balance control layer, the electron transport layer, and the electron injection layer may be deposited using a single-molecule deposition process or a solution process.

Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

A better understanding of the light-emitting diode according to the present disclosure may be obtained through the following examples which are set forth to illustrate, but are not to be construed as limiting the present disclosure.

EXAMPLES

Preparation Examples of Compounds for Charge Balance Control Layer

Synthesis Example 1

Synthesis of Compound 7

Synthesis Example 1-(1)

Synthesis of Intermediate 1-a

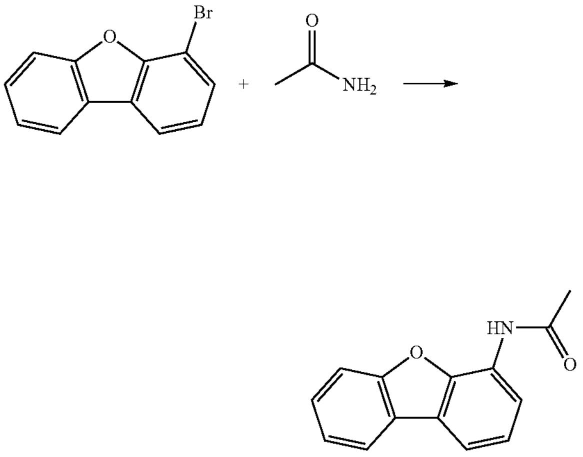

<Intermediate 1-a>

In a 2-L round bottom flask, 4-bromodibenzofuran (150.0 g, 0.607 mol), acetamide (53.8 g, 0.911 mol), copper iodide (57.8 g, 0.30 mol), (±)trans-1,2-diaminocyclohexane (63.9 g, 0.60 mol), potassium carbonate (167.8 g, 1.21 mol), and toluene (1500 ml) were stirred together overnight under reflux. After completion of the reaction, filtration was conducted through a silica gel pad. The filtrate was washed many times with toluene and concentrated in a vacuum. The concentrate was crystalized in acetonitrile to afford <Intermediate 1-a> as a crystal (70.0 g, 51%).

Synthesis Example 1-(2)

Synthesis of Intermediate 1-b

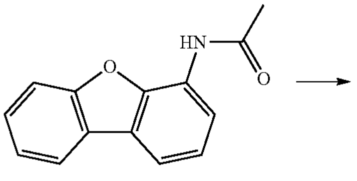

<Intermediate 1-a>

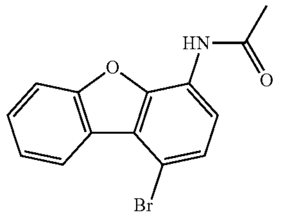

<Intermediate 1-b>

In a 2-L round-bottom flask reactor, Intermediate 1-a (70.0 g, 0.311 mol) was dissolved in acetic acid (630 ml). A mixture of bromine (49.7 g, 0.311 mol) and acetic acid (280 ml) was dropwise added into the reactor. At room temperature, the mixture was stirred for 2 hours. After completion of the reaction, water (100 ml) was added and stirred. The gray solid thus formed was slurried in ethanol (500 ml), stirred, and filtered. Dehydration of the filtrate afforded <Intermediate 1-b>. (86.0 g, 91%)

Synthesis Example 1-(3)

Synthesis of Intermediate 1-c

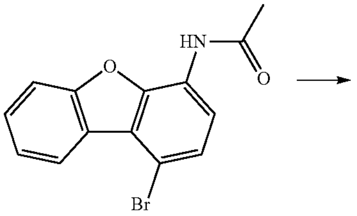

<Intermediate 1-b>

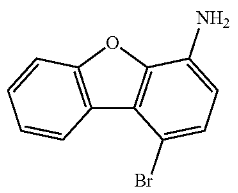

<Intermediate 1-c>

In a 2-L round-bottom flask reactor, <Intermediate 1-b> (86.0 g, 0.283 mol) was dissolved in ethanol (600 ml) and tetrahydrofuran (430 ml) and stirred. A solution of potassium hydroxide (47.6 g, 0.848 mol) in water (260 ml) was slowly added to the reactor, followed by stirring overnight under reflux. After completion of the reaction, the reaction mixture was cooled to room temperature. Extraction with ethyl acetate and water gave an organic layer which was then concentrated in a vacuum. The concentrate was stirred in excess ethanol and filtered. Recrystallization in methylene chloride and heptane afforded <Intermediate 1-c>. (73.0 g, 98%)

Synthesis Example 1-(4)

Synthesis of Intermediate 1-d

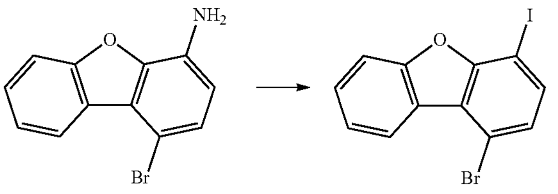

<Intermediate 1-c> <Intermediate 1-d>

In a 2-L round-bottom flask reactor, a mixture of Intermediate 1-c (73.0 g, 0.279 mol), HCl (90 ml), and water (440 ml) was cooled to 0° C. and stirred. At the same temperature, a solution of sodium nitrite (25.0 g, 0.362 mol) in water (90 ml) was dropwise added and then stirred for 1 hour. A solution of potassium iodide (92.5 g, 0.557 mol) in water (90 ml) was dropwise added to the reaction solution and then stirred at room temperature. After completion of the reaction, the reaction mixture was extracted with ethylacetate and water. The organic layer was washed with an aqueous sodium thiosulfate pentahydrate solution, separated, and concentrated in a vacuum. Purification by column chromatography afforded Intermediate 1-d (52.3 g, 50.3%).

Synthesis Example 1-(5)

Synthesis of Intermediate 1-e

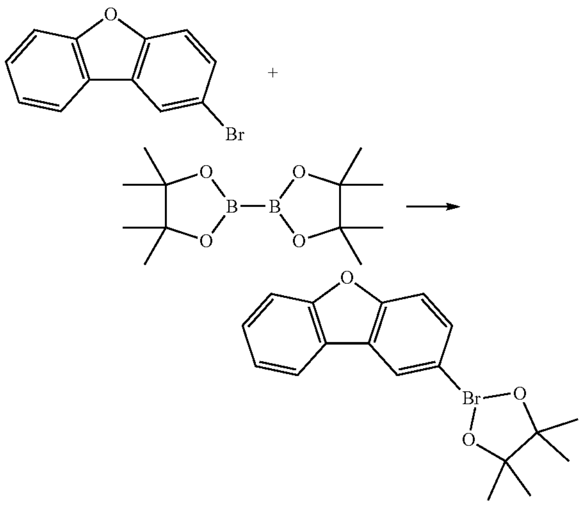

<Intermediate 1-e>

In a 2-L round-bottom flask reactor, 2-bromodibenzofuran (70.0 g, 0.283 mmol), bis(pinacolato)diboron (286.3 g, 0.340 mol), 1,1'-bis(diphenylphosphino)ferrocene-palladium (II) dichloride (4.6 g, 0.006 mol), potassium acetate (56.6 g, 0.567 mol), and 1,4-dioxane (700 ml) were stirred together overnight under reflux. After completion of the reaction, filtration was performed through a celite pad. The filtrate was concentrated in a vacuum and purified by column chromatography to afford Intermediate 1-e. (66.4 g, 79%).

Synthesis Example 1-(6)

Synthesis of Intermediate 1-f

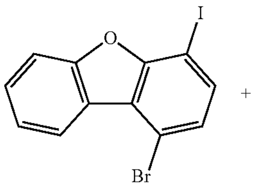

<Intermediate 1-d>

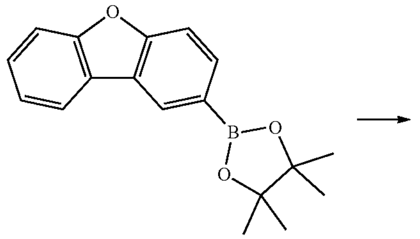

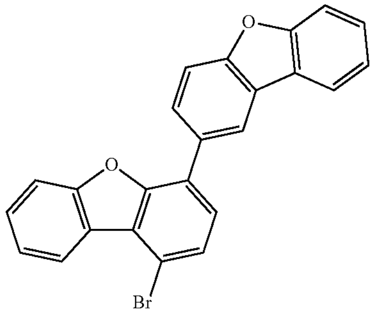

<Intermediate 1-f>

In a 2-L round-bottom flask reactor, Intermediate 1-d (15.0 g, 40 mmol), Intermediate 1-e (12.9 g, 44 mmol), tetrakis(triphenylphosphine)palladium (0.9 g, 1 mmol), and potassium carbonate (11.1 g, 80 mmol) were placed, followed by adding toluene (100 mL), methanol (45 mL), and water (30 mL). The mixture was stirred overnight under reflux. After completion of the reaction, the reactor was cooled to room temperature. Then, the reaction mixture was extracted with ethyl acetate and the organic layer thus formed was concentrated in a vacuum. Column chromatography isolated a solid which was then recrystallized in heptane to afford Intermediate 1-f. (8.9 g, 53.9%)

Synthesis Example 1-(7)

Synthesis of Compound 7

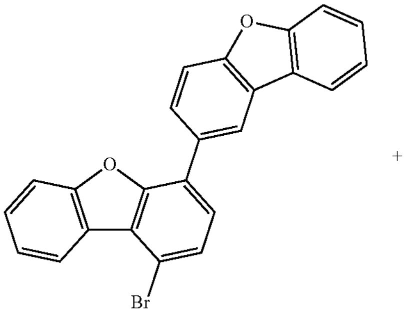

<Intermediate 1-f>

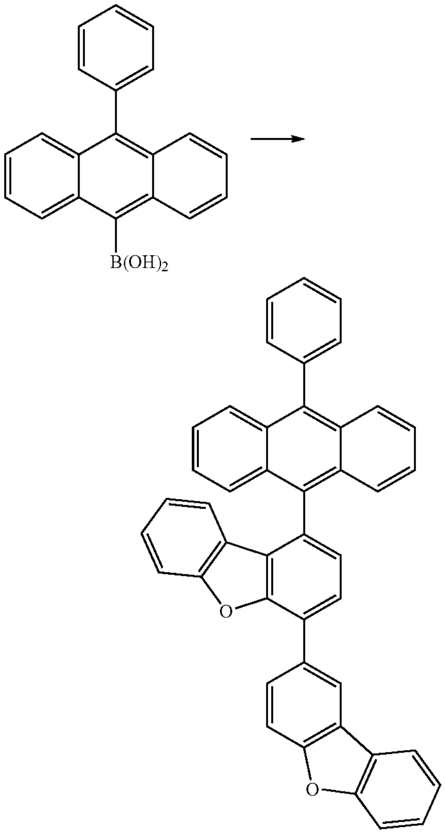

<Compound 7>

In a 250-mL round-bottom flask reactor, Intermediate 1-f (9.1 g, 22 mmol), 10-phenyl-anthracene-9-boronic acid (7.7 g, 26 mmol), tetrakis(triphenylphosphine)palladium (0.5 g, 1 mmol), and potassium carbonate (6.0 g, 43 mmol) were placed, followed by adding toluene (50 mL), ethanol (21 mL), and water (14 mL). The reactor was heated to 90° C. and the mixture was stirred overnight. After completion of the reaction, the reactor was cooled to room temperature. The reaction mixture was added with methanol (50 ml) and stirred at room temperature. The solid thus formed was filtered and washed with methanol. The solid was recrystallized in toluene and acetone to afford Compound 7. (6.1 g, 47%)

MS (MALDI-TOF): m/z 586.19 [W]

Synthesis Example 2

Synthesis of Compound 67

Synthesis Example 2-(1)

Synthesis of Compound 67

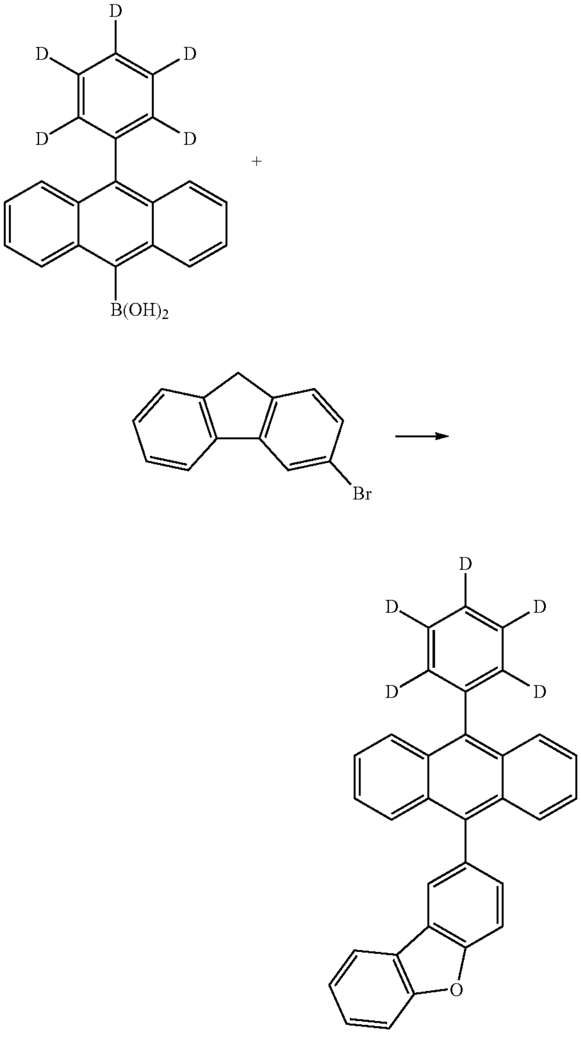

<Compound 67>

In a 500-mL round-bottom flask reactor, 10-phenyl(d5)-anthracene-9-boronic acid (38.6 g, 127 mmol), 2-bromodibenzofuran (26.2 g, 106 mmol), tetrakis(triphenylphosphine)palladium (3.43 g, 3 mmol), and potassium carbonate (27.35 g, 197.9 mmol) were placed, followed by adding toluene (150 mL), tetrahydrofuran (150 mL), and water (60 mL). The reactor was heated to 90° C. and the mixture was stirred overnight. After completion of the reaction, the reactor was cooled to room temperature, extraction with ethyl acetate gave an organic layer which was then isolated and concentrated in a vacuum. Purification by column chromatography afforded Compound 67. (34.1 g, 75.7%)

MS (MALDI-TOF): m/z 425.18 [W]

Synthesis Example 3

Synthesis of Compound 68

Synthesis Example 3-(1)

Synthesis of Intermediate 3-a

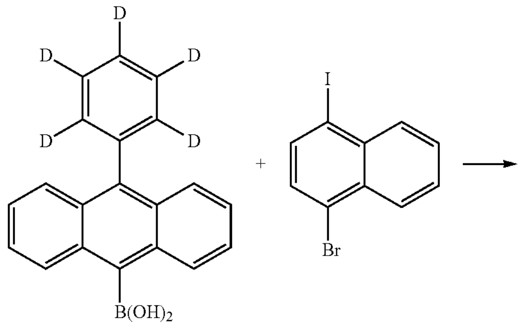

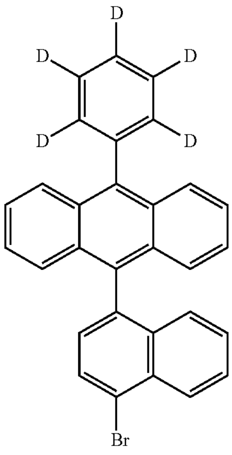

<Intermediate 3-a>

In a 500-mL round-bottom flask reactor, 10-phenyl(d5)-anthracene-9-boronic acid (38.6 g, 127 mmol), 1-bromo-4-iodonaphthalene (35.3 g, 106 mmol), tetrakis(triphenylphosphine)palladium (3.43 g, 3 mmol), and potassium carbonate (27.35 g, 197.9 mmol) were placed, followed by adding toluene (150 mL), tetrahydrofuran (150 mL), and water (60 mL). The reactor was heated to 90° C. and the mixture was stirred overnight. After completion of the reaction, the reaction mixture was cooled to room temperature and extracted with ethyl acetate. The organic layer thus formed was separated, concentrated in a vacuum, and purified by column chromatography to afford Intermediate 3-a. (39.2 g, 79.7%)

Synthesis Example 3-(2)

Synthesis of Compound 68

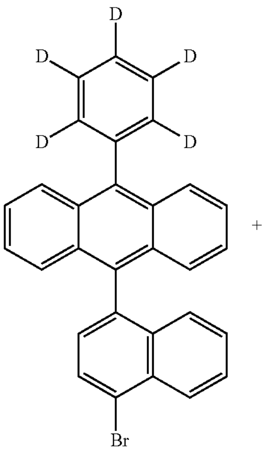

<Intermediate 3-a>

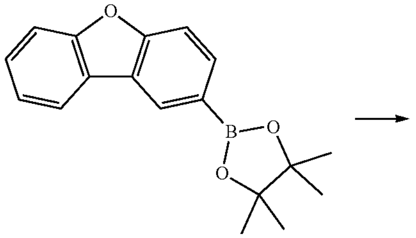

<Intermediate 1-e>

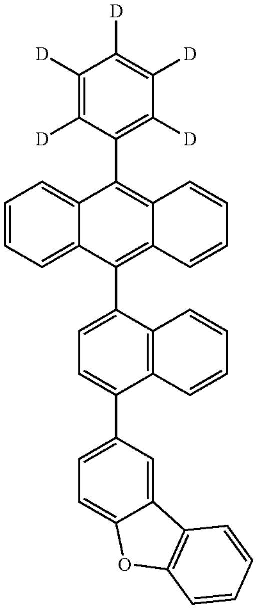

<Compound 68>

The same procedure as in Synthesis Example 1-(7) was conducted, with the exception of using Intermediate 1-e and Intermediate 3-a instead of 10-phenyl-anthracene-9-boronic acid Intermediate 1-f, respectively, to afford Compound 68. (8.5 g, 66.5%).

MS (MALDI-TOF): m/z 551.23 [W]

Preparation Examples of Compound for Dopant in Light-Emitting layer

Synthesis Example 4

Synthesis of Compound 125

Synthesis Example 4-(1)

Synthesis of Intermediate 4-a and Intermediate 4-b

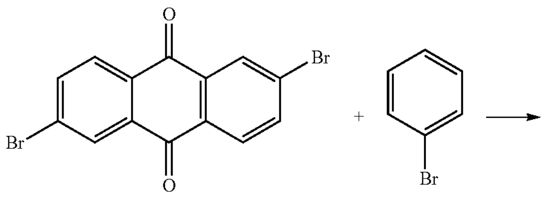

[Intermediate 4-a]

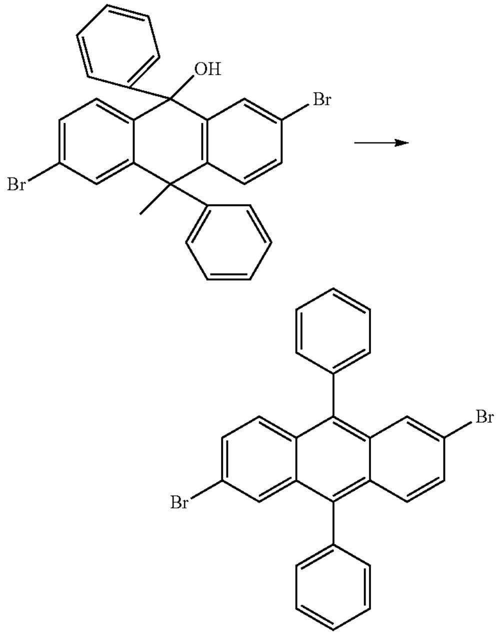

[Intermediate 4-b]

In a 1-L round-bottom flask, a mixture of bromobenzene (44.3 g, 0.282 mol) and THF (250 ml) was cooled to −78° C. and then slowly added with drops of n-butyl lithium (163 ml, 0.261 mol). At the same temperature, the mixture was stirred for 1 hour before the addition of 2,6-dibromoanthraquinone (30 g, 0.104 mol). The reaction mixture was heated to room temperature before being stirred for 12 hours. Then, 2N HCl (300 ml) was added. Layer separation gave Intermediate 4-a.

In a 1-L round-bottom flask, Intermediate 4-a was cooled together with KI (52 g, 0.313 mol), $NaH_2PO_2$—$H_2O$ (66.5 g, 0.627 mol), and acetic acid (600 ml) for 5 hours under reflux. The reaction mixture was cooled to room temperature, filtered, and washed with excess water and methanol. Recrystallization in toluene afforded Intermediate 4-b. (19 g, 45%)

Synthesis Example 4-(2)

Synthesis of Intermediate 4-c

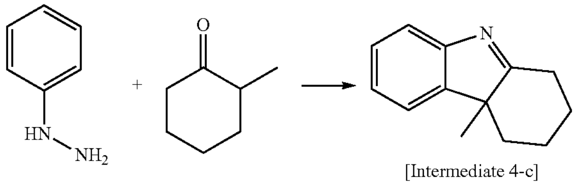

[Intermediate 4-c]

In a 500-ml round-bottom flask, phenylhydrazine (40 g, 0.3699 mol), 2-methylcyclohexanone (41.5 g, 0.3699 mol), and acetic acid (240 ml) were refluxed for 6 hours. After completion of the reaction, the reaction mixture was alkalinized with sodium hydroxide, extracted with water and ethylene acetate, and neutralized. The organic layer was dehydrated over magnesium sulfate, concentrated, and isolated by column chromatography to afford Intermediate 4-c. (57.5 g, 84%)

Synthesis Example 4-(3)

Synthesis of Intermediate 4-d

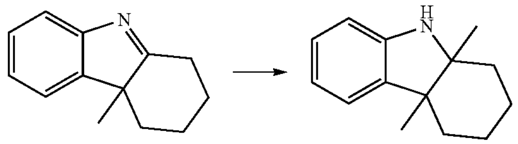

[Intermediate 4-d]

In a 500-ml round-bottom flask, Intermediate 4-c (50 g, 0.27 mol) was dissolved in toluene (150 ml) under a nitrogen atmosphere and cooled to −20° C. Drops of 1.6M methyl lithium (260 ml, 0.1753 mol) were slowly added to the solution, followed by reaction for 3 hours at −20° C. After completion of the reaction, the reaction mixture was slowly added with 200 ml of a 1:1 solution of toluene and water. The organic layer thus formed was concentrated in a vacuum. Column chromatographic purification afforded Intermediate 4-d (47.3 g, 87%).

Synthesis Example 4-(4)

Synthesis of Compound 125

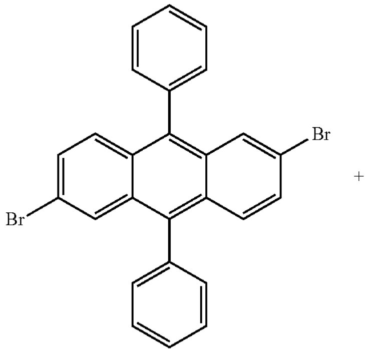

-continued

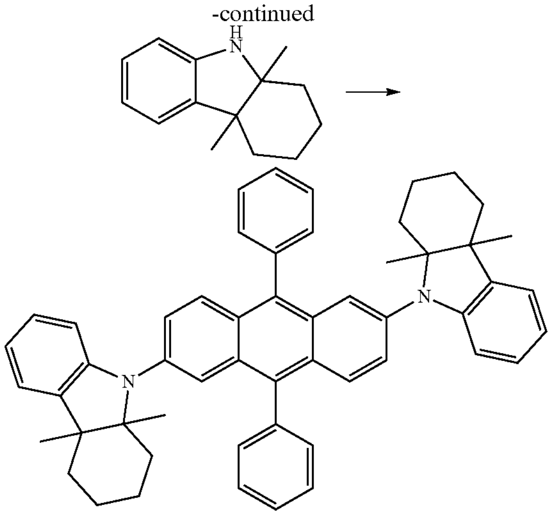

[Compound 125]

In a 250-ml round-bottom flask, Intermediate 4-b (10 g, 0.0205 mol), Intermediate 4-d (9.9 g, 0.0492 mol), palladium acetate (0.18 g, 0.82 mmol), BINAP (0.51 g, 0.82 mmol), sodium tert-butoxide (7.8 g, 0.082 mol), and toluene (80 ml) were placed and refluxed for 12 hours. After completion of the reaction, the reaction mixture in a hot state was filtered through celite on a Büchner funnel. Recrystallization in toluene afforded Compound 125 as a pale solid. (3.4 g, 19.7%)

MS (MALDI-TOF): m/z 728.41 [W]

Synthesis Example 5

Synthesis of Compound 126

The same procedure as in Synthesis Example 4, with the exception of using 4-methyl bromobenzene instead of bromobenzene, to afford Compound 126. (22.8%)

MS (MALDI-TOF): m/z 756.44 [W]

Synthesis Example 6

Synthesis of Compound 129

The same procedure as in Synthesis Example 4, with the exception of using 4-tert-butyl bromobenzene instead of bromobenzene, to afford Compound 129. (19.7%)

MS (MALDI-TOF): m/z 840.54 [W]

Synthesis Example 7

Synthesis of Compound 130

The same procedure as in Synthesis Example 4, with the exception of using 1-bromo-p-biphenyl instead of bromobenzene, to afford Compound 130. (23.4%)

MS (MALDI-TOF): m/z 880.48 [W]

Examples 1-10

Fabrication and Evaluation of Organic Light-Emitting Diode

An ITO glass substrate was patterned to have a luminescent area of 2 mm×2 mm and cleansed. The ITO glass was mounted in a vacuum chamber that was then set to have a base pressure of $1\times10^{-7}$ torr. On the ITO glass substrate, films of DNTPD (700 Å) and α-NPD (300 Å) were formed in that order. A light-emitting layer (200 Å) was formed of a mixture of GH as a host and one of the compounds listed in Table 1 as a dopant (weight ratio 97:3). Then, each of the compounds shown in Table 1 was deposited to form a charge balance control layer (50 Å), on which [Chemical Formula E-1] for an electron transport layer (250 Å), [Chemical Formula E-2] for an electron injection layer (5 Å), and Al (1000 Å) were deposited in the order to fabricate an organic light-emitting diode.

The diodes of the Examples and the Comparative Examples were measured for luminance reduction rates in a low dynamic range. In this regard, voltages of from −2 V to 6 V were applied at regular intervals of 0.2 V to the diodes while EL emission spectra were obtained using a spectroradiometer (SR3A: manufactured by TOPCON). From the spectral radiant luminance spectrum, chromaticity coordinates (CIE_x, CIE_y), external quantum efficiency, and luminance were measured.

Luminance reduction rates in a low dynamic range are given in Table 1, below.

[DNTPD]

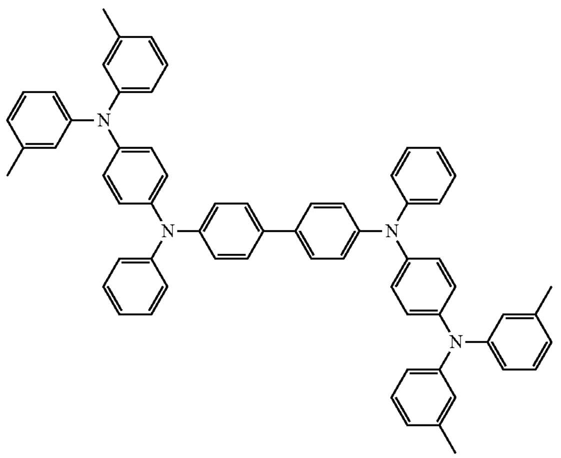

[α-NPD]

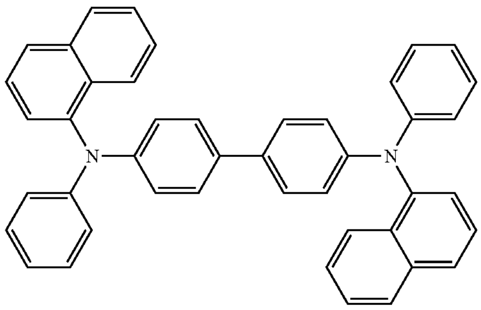

-continued

[GH]

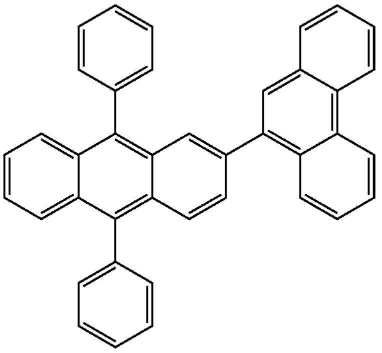

[Chemical Formula E-1]

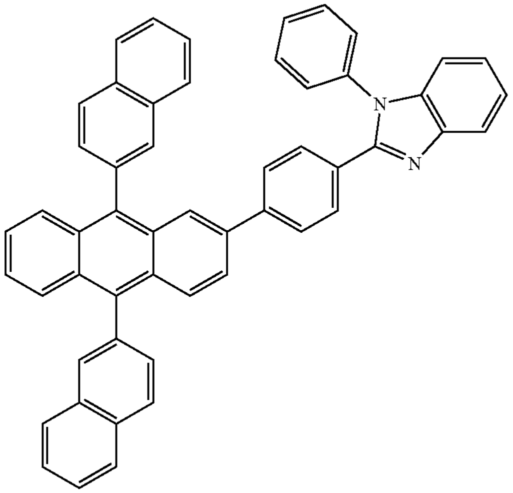

[Chemical Formula E-2]

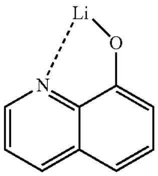

Comparative Example 1 to 4

Organic light-emitting diodes were fabricated in the same manner as in Examples 1 to 10, with the exception that an electron transport layer was formed of Compound of Chemical Formula E-1 at a thickness of 300 Å instead of the formation of a charge balance control layer.

TABLE 1

| | Dopant | Charge Balance Control Layer | CIEx | CIEy | El (λmax) (nm) | Luminance Reduction Rate in Low Dynamic Range (%) |
|---|---|---|---|---|---|---|
| C. Ex. 1 | Cpd. 125 | | 0.259 | 0.653 | 520 | -42.9 |
| Ex. 1 | Cpd. 125 | Cpd. 7 | 0.260 | 0.653 | 520 | -3.7 |
| Ex. 2 | Cpd. 125 | Cpd. 67 | 0.260 | 0.654 | 521 | -2.9 |
| Ex. 3 | Cpd. 125 | Cpd. 68 | 0.260 | 0.654 | 520 | -4.2 |
| C. Ex. 2 | Cpd. 126 | — | 0.249 | 0.651 | 519 | -37.2, -12.5 |
| Ex. 4 | Cpd. 126 | Cpd. 7 | 0.250 | 0.651 | 519 | -4.2 |
| Ex. 5 | Cpd. 126 | Cpd. 68 | 0.250 | 0.652 | 519 | -4.2 |
| C. Ex. 3 | Cpd. 129 | — | 0.240 | 0.652 | 517 | -49 |
| Ex. 6 | Cpd. 126 | Cpd. 7 | 0.240 | 0.653 | 517 | -2.3 |

TABLE 1-continued

| | Dopant | Charge Balance Control Layer | CIEx | CIEy | El (λmax) (nm) | Luminance Reduction Rate in Low Dynamic Range (%) |
|---|---|---|---|---|---|---|
| Ex. 7 | Cpd. 129 | Cpd. 68 | 0.241 | 0.654 | 518 | -3.2 |
| C. Ex. 4 | Cpd. 130 | | 0.248 | 0.654 | 518 | -37.1 |
| Ex. 8 | Cpd. 130 | Cpd. 7 | 0.249 | 0.655 | 519 | -2.3 |
| Ex. 9 | Cpd. 130 | Cpd. 67 | 0.248 | 0.655 | 518 | -1.1 |
| Ex. 10 | Cpd. 130 | Cpd. 68 | 0.248 | 0.655 | 519 | -4.5 |

Characteristics of the organic light-emitting diodes fabricated as indicated in Table 1 according to the Examples and Comparative Examples are depicted in FIGS. 3 to 6.

In FIGS. 3 to 6, the x axis represents inverse values of current density (J), showing a lower dynamic range at a more right point while the y axis represents relative luminance reduction slopes based on the maximum. A smaller luminance reduction slope means smaller reduction in color reproducibility in the overall current density range.

As can be seen in Table 1 and FIGS. 3 to 6, the organic light-emitting diodes according to the present disclosure are remarkably low in luminance reduction rate in a low dynamic range, compared to those of the Comparative Examples. Therefore, the present disclosure can provide an organic light-emitting diode having improved efficiency.

INDUSTRIAL APPLICABILITY

Providing a light-emitting diode having alleviated luminance reduction rates in a low dynamic range, the present invention is industrially applicable.

The invention claimed is:

1. An organic light-emitting diode comprising:

a first electrode;

a second electrode facing the first electrode; and a light-emitting layer and a charge balance control layer arranged sequentially between the first and the second electrode, wherein the first electrode and the second electrode serve as an anode and a cathode, respectively, and a hole transport layer and an electron transport layer are arranged between the anode and the light-emitting layer and between the charge balance control layer and the cathode, respectively, the light-emitting layer includes a host and a dopant and an anthracene compound represented by Chemical Formula A serves as the dopant, the affinity $A_{ed}$ (eV) of the charge balance control layer falls between the affinity $A_h$ (eV) of the host in the light-emitting layer and the affinity $A_e$ (eV) of the electron transport layer ($A_h \geq A_{ed} \geq A_e$), and the charge balance control layer includes at least one of anthracene derivative compounds represented by the following Chemical Formula B or C:

[Chemical Formula A]

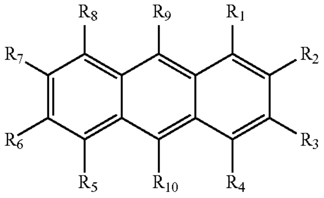

wherein, $R_1$ to $R_8$ may be the same or different and are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted alkylsilyl of 1 to 30 carbon atoms, a substituted or unsubstituted arylsilyl of 6 to 30 carbon atoms, a cyano, a nitro, and a halogen, with a proviso that one or two of $R_1$ to $R_8$ is a substituent represented by the following Structural Formula A or B:

[Structural Formula A]

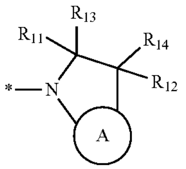

[Structural Formula B]

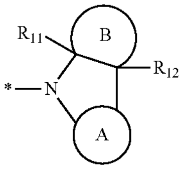

wherein, the ring moiety A is a substituted or unsubstituted aromatic hydrocarbon ring of 6 to 12 carbon atoms, and the ring moiety B of Structural Formula B is a substituted or unsubstituted cycloalkylene of 2 to 8 carbon atoms, $R_9$ and $R_{10}$ in Chemical Formula A may be same or different and are each independently a substituted or unsubstituted aryl of 6 to 18 carbon atoms, $R_{11}$ to $R_{14}$ may be the same or different and are each independently selected from the group consisting of a hydrogen atom, a deuterium atom, a substituted or unsubstituted alkyl of 1 to 30 carbon atoms, a substituted or unsubstituted cycloalkyl of 3 to 30 carbon atoms, a substituted or unsubstituted aryl of 6 to 30 carbon atoms, a substituted or unsubstituted aralkyl of 7 to 30 carbon atoms, a cyano, and a halogen,

* denotes a bonding site to the anthracene moiety, and when the anthracene moiety has plural substituents of Structural Formula A or B attached thereon, they may be the same or different; and

[Chemical Formula B]

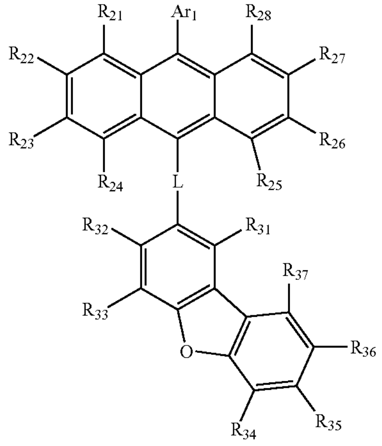

[Chemical Formula C]

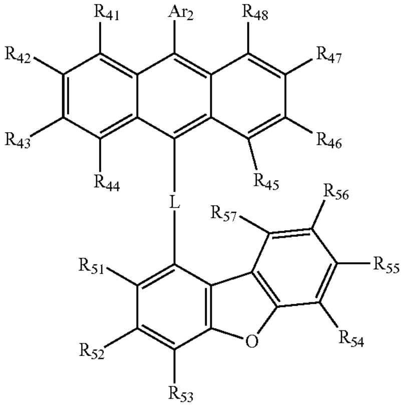

wherein, in Chemical Formula B, $R_{21}$ to $R_{28}$ may be the same or different and are each independently selected from among a hydrogen atom, a deuterium atom, and a substituted or unsubstituted alkyl of 1 to 30 carbon atoms, $R_{31}$ to $R_{37}$ may be the same or different and are each independently selected from among a hydrogen atom and a deuterium atom, in Chemical Formula C, $R_{41}$ to $R_{48}$ may be the same or different and are each independently selected from among a hydrogen atom, a deuterium atom, and a substituted or unsubstituted alkyl of 1 to 30 carbon atoms, $R_{51}$ to $R_{57}$ may be the same or different and are each independently selected from among a hydrogen atom and a deuterium atom, in Chemical Formula B and Chemical Formula C, $Ar_1$ and $Ar_2$ are each independently a substituted or unsubstituted aryl of 6 carbon atoms or a substituted or unsubstituted aryl of 10 carbon atoms; and L is a single bond or one selected from among the following Structural Formulas 1 and 2:

[Structural Formula 1]

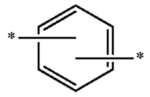

-continued

[Structural Formula 2]

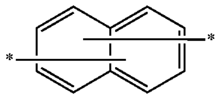

wherein each of the unsubstituted carbon atoms of the aromatic ring moiety is bound with a hydrogen atom or a deuterium atom, wherein the term ‘substituted’ of the expression “substituted or unsubstituted” used with Chemical Formulas A to C means having at least one substituent selected from the group consisting of a deuterium atom, a cyano, a halogen, a nitro, and an alkyl of 1 to 24 carbon atoms.

2. The organic light-emitting diode of claim 1, wherein none or one of the substituents $R_1$ to $R_4$ in Chemical Formula A is the substituent of Structural Formula A or B and none or one of the substituents $R_5$ to $R_8$ in Chemical Formula A is the substituent of Structural Formula A or B.

3. The organic light-emitting diode of claim 1, wherein the compound represented by Chemical Formula B or C is one selected from the group consisting of the following Compounds:

<Compound 1>

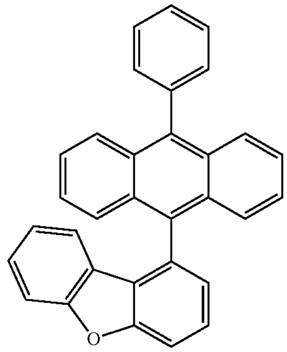

<Compound 12>

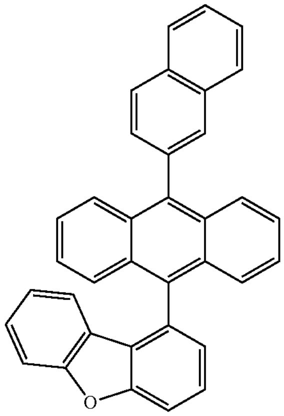

-continued

<Compound 31>

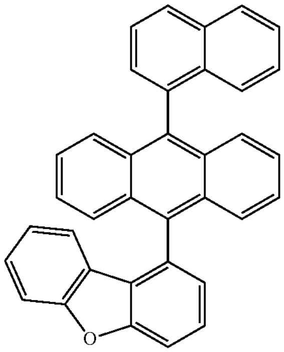

<Compound 55>

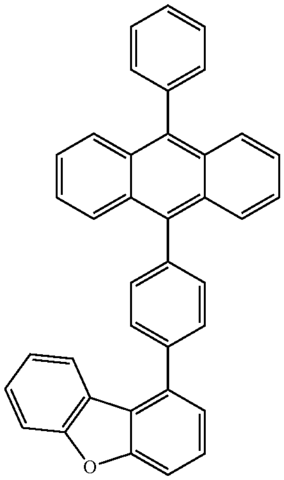

<Compound 60>

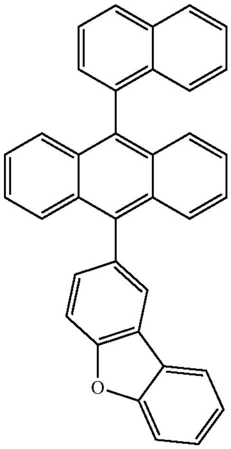

-continued
<Compound 67>
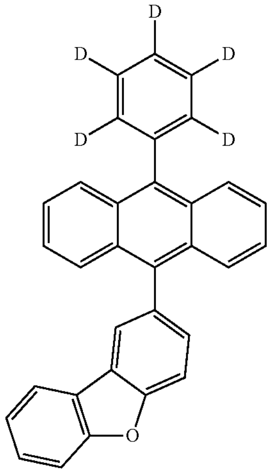
<Compound 68>
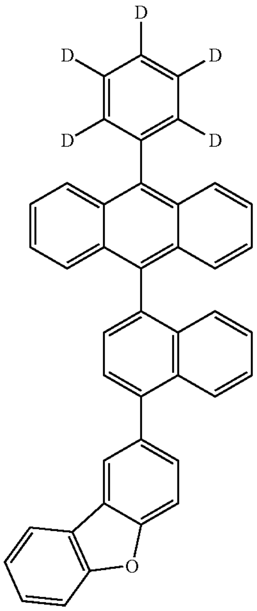
-continued
<Compound 70>
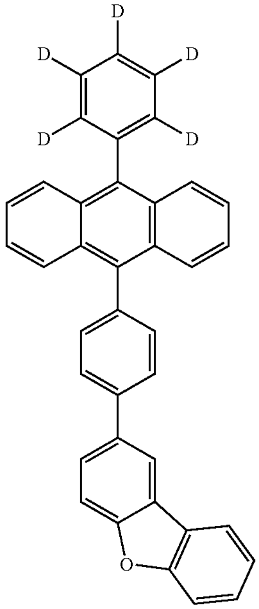
<Compound 73>
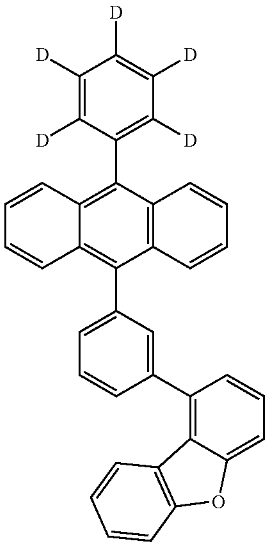
.
4. The organic light-emitting diode of claim 1, wherein the compound represented by Chemical Formula A is one selected from the group consisting of the following Compounds 101 to 139:

-continued
<Compound 101>
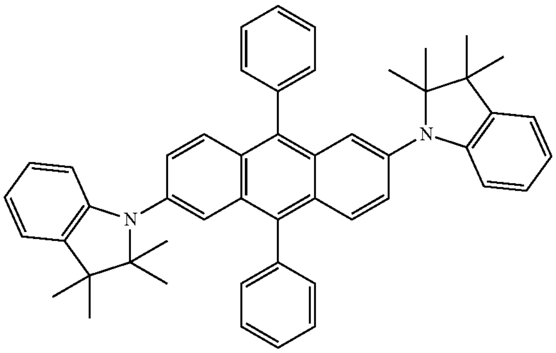
<Compound 102>
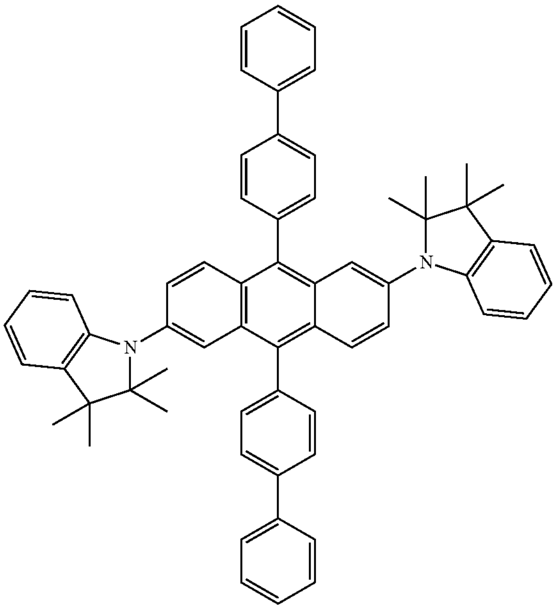
<Compound 103>
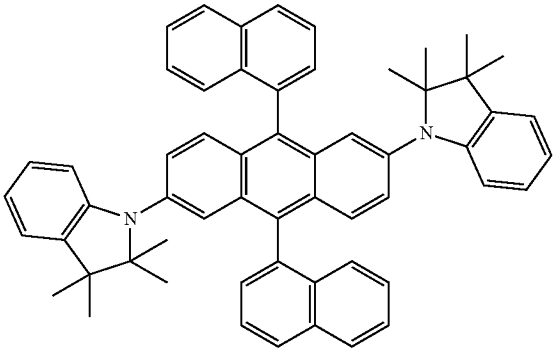
<Compound 104>
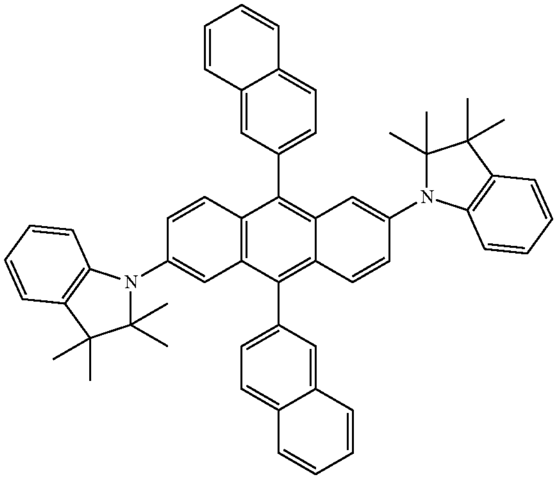
<Compound 105>
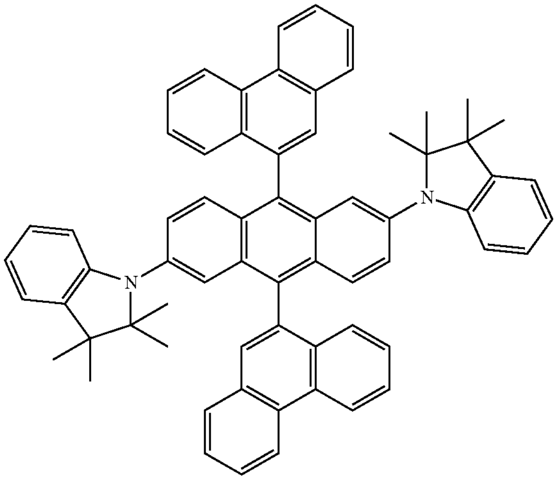
<Compound 106>
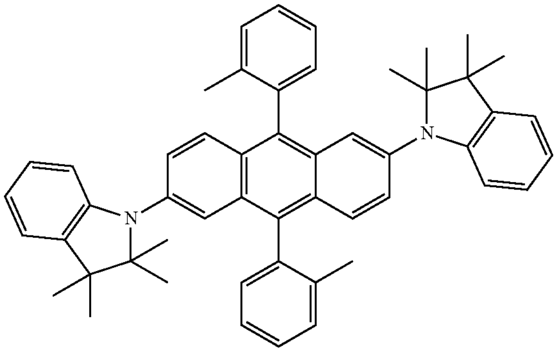

-continued
<Compound 107>
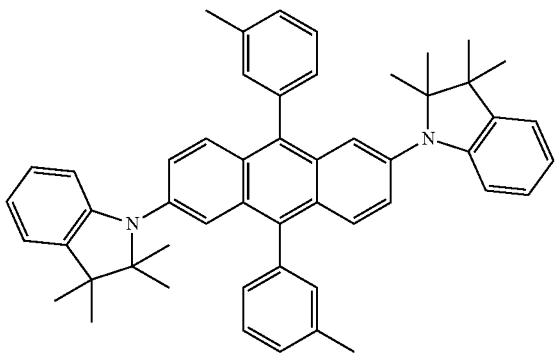
<Compouond 108>
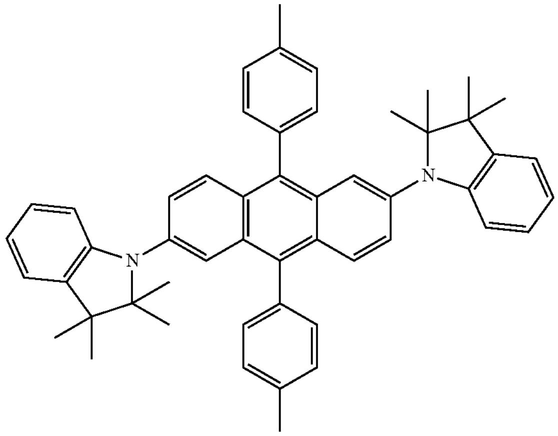
<Compound 109>
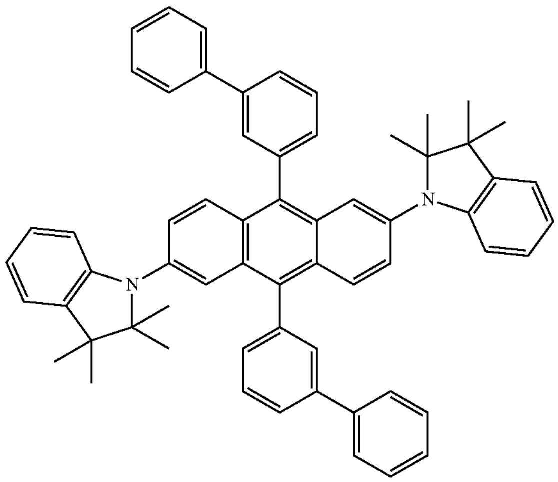
-continued
<Compound 110>
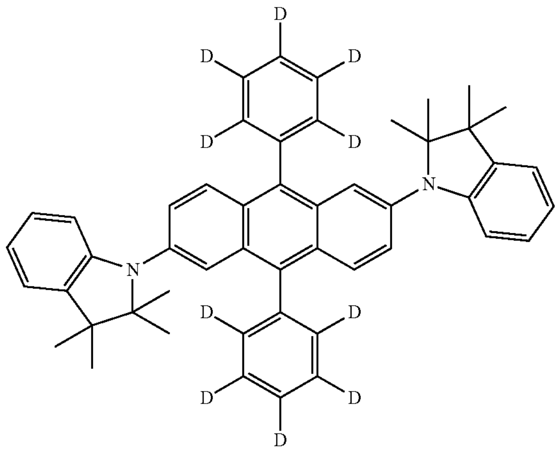
<Compound 111>
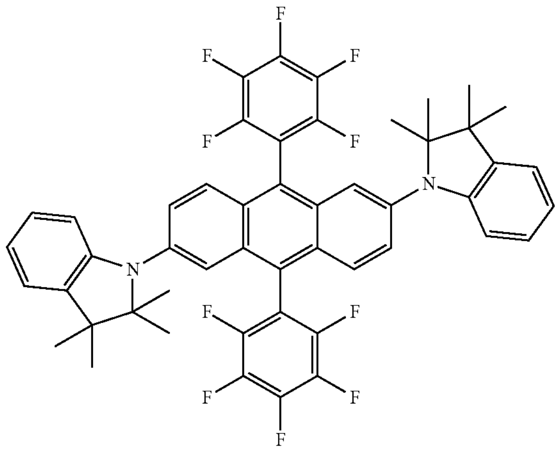
<Compound 112>
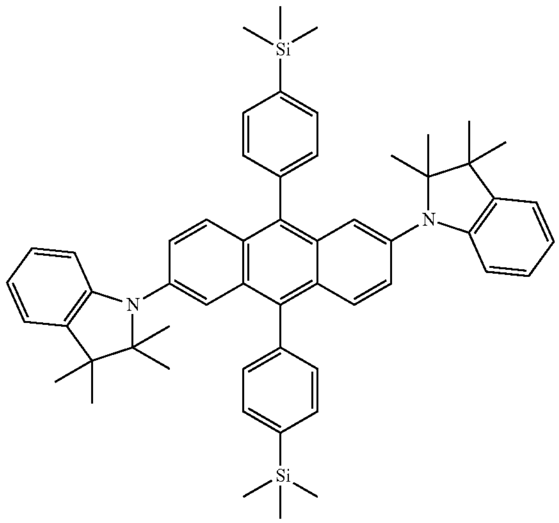

<Compound 113>
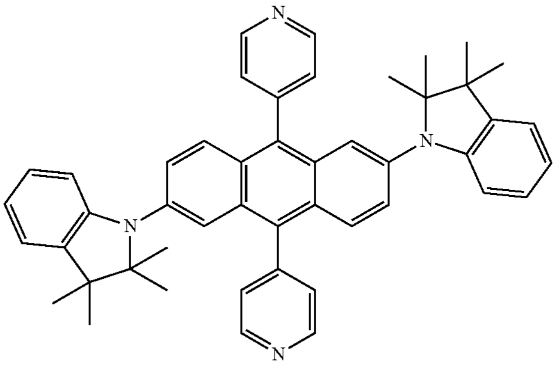
<Compound 114>
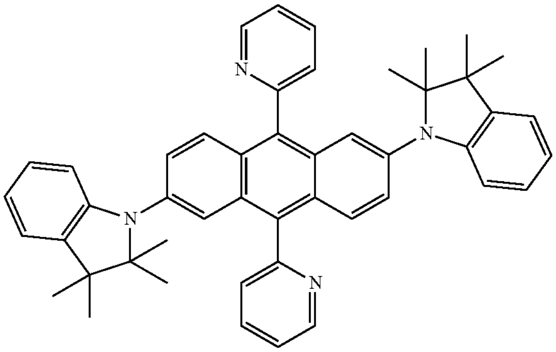
<Compound 115>
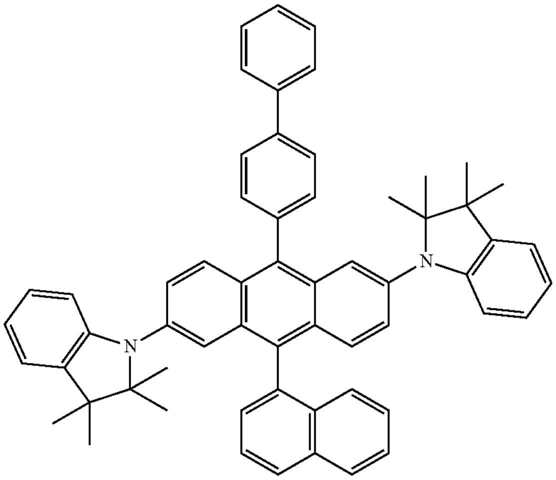
<Compound 116>
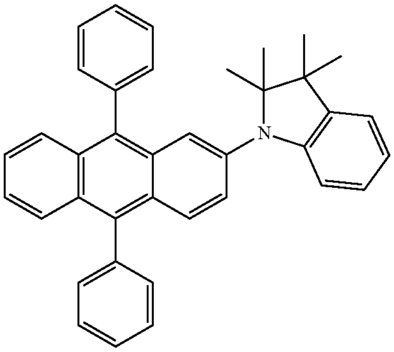
<Compound 117>
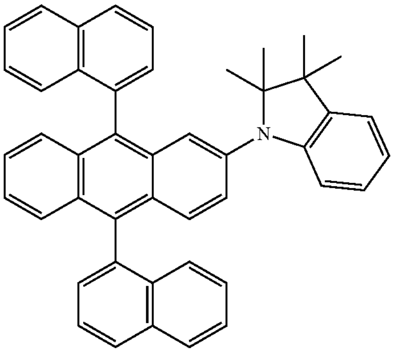
<Compound 118>
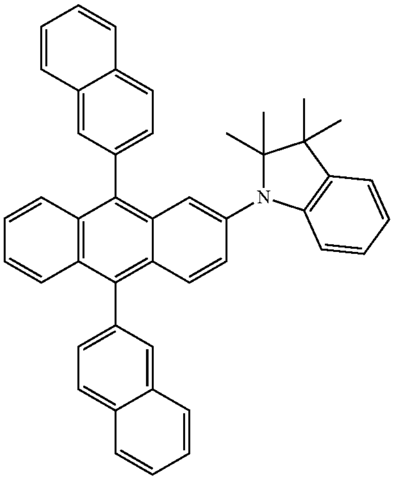
<Compound 119>
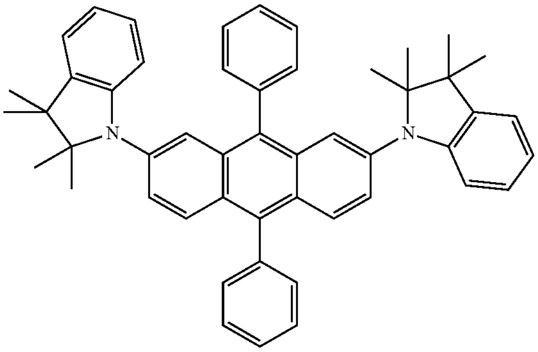

-continued
<Compound 120>
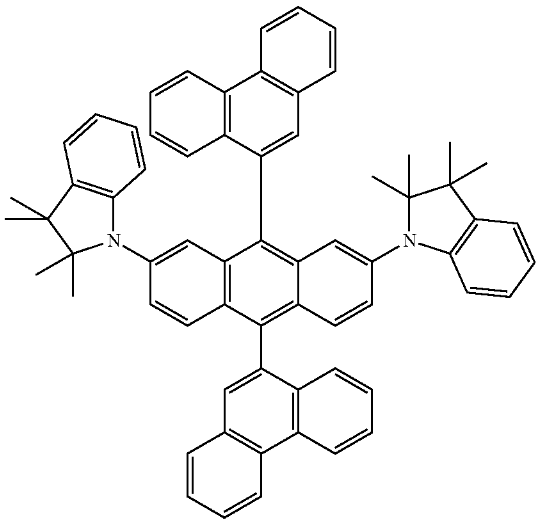
<Compound 121>
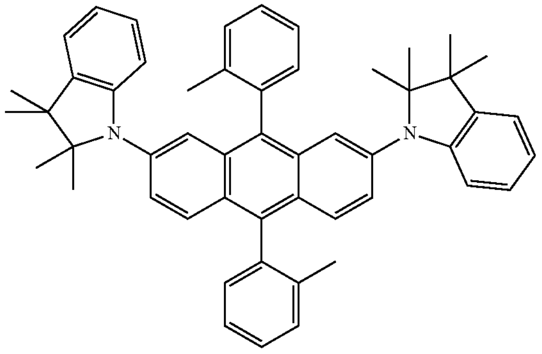
<Compound 122>
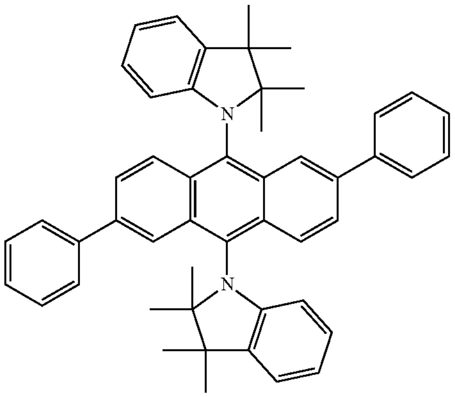
-continued
<Compound 123>
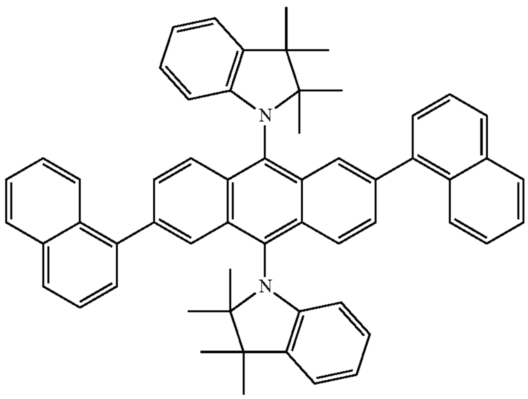
<Compound 124>
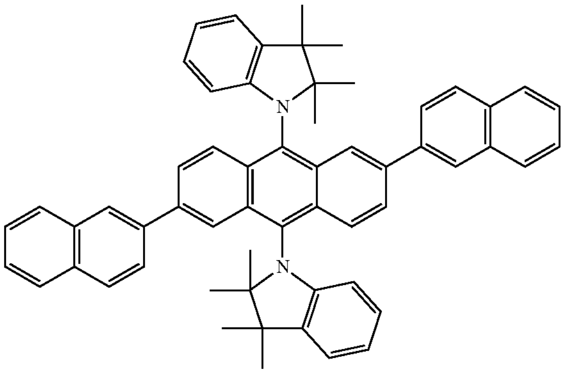
<Compound 125>
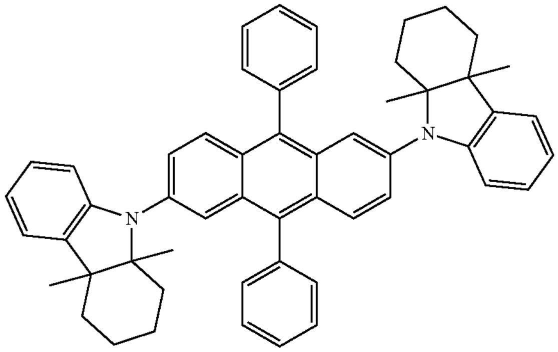
<Compound 126>
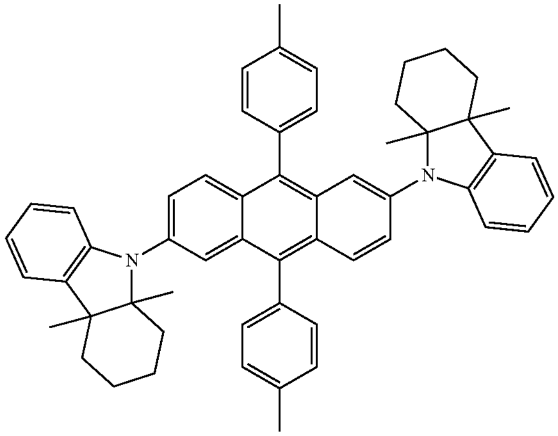

-continued
<Compound 127>
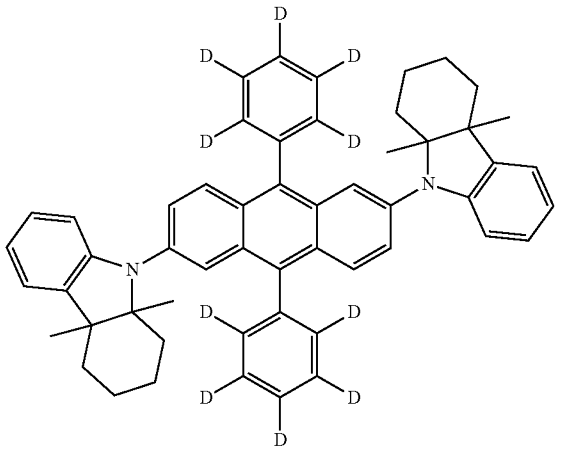
<Compound 128>
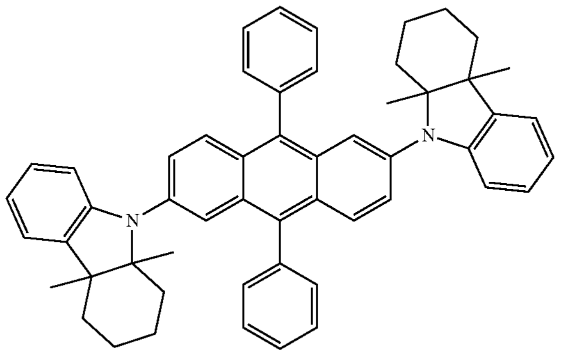
<Compound 129>
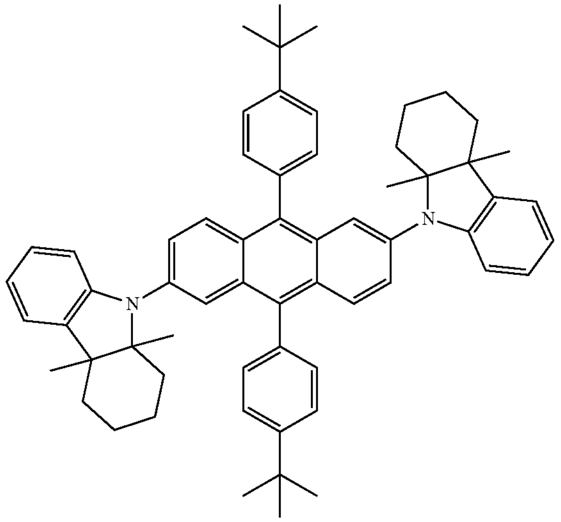
-continued
<Compound 130>
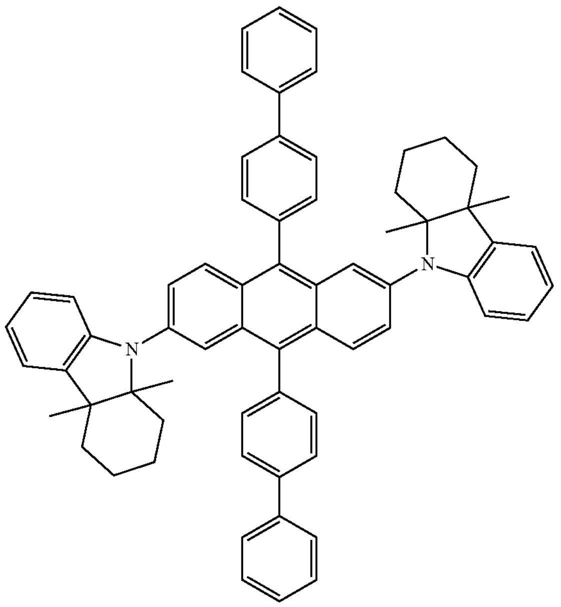
<Compound 131>
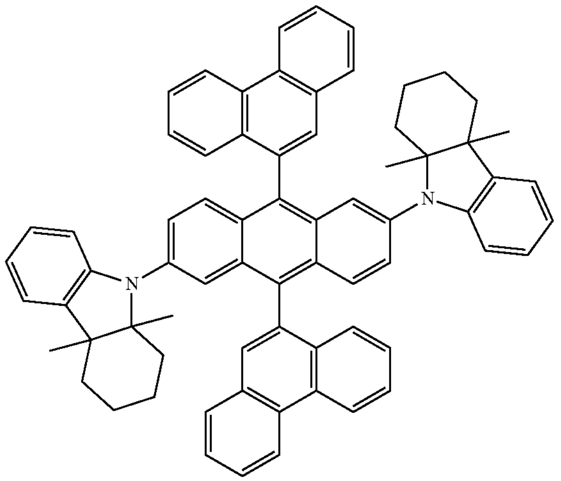
<Compound 132>
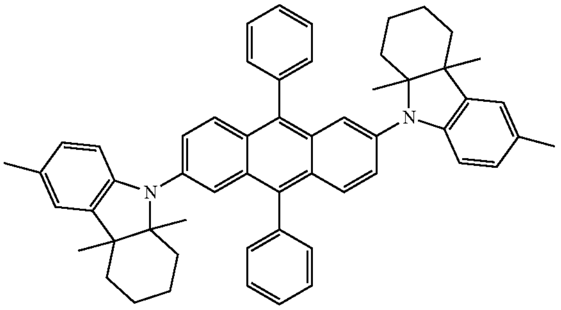

-continued
<Compound 133>
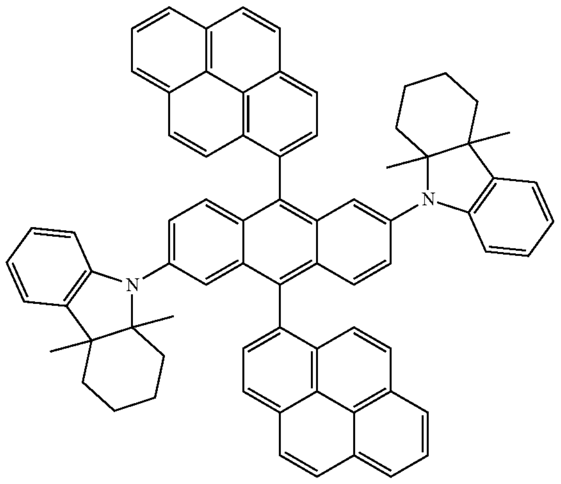
<Compound 134>
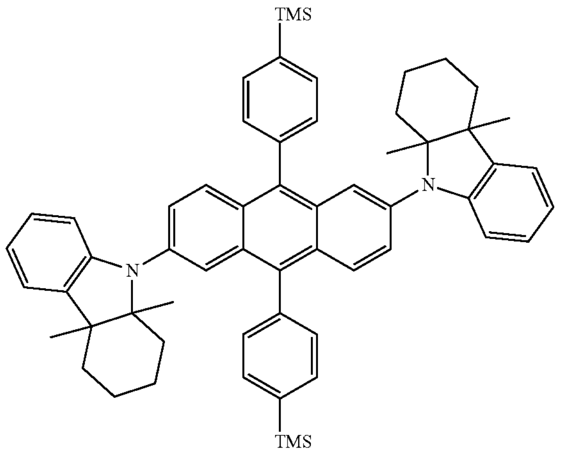
<Compound 135>
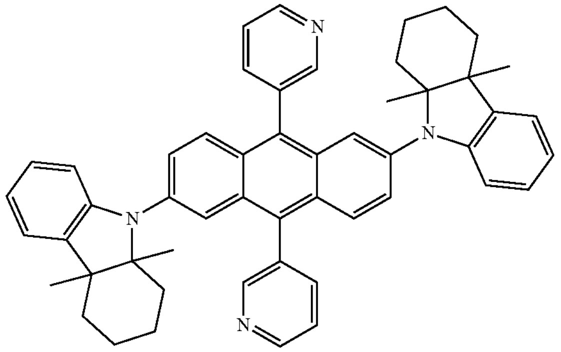
-continued
<Compound 136>
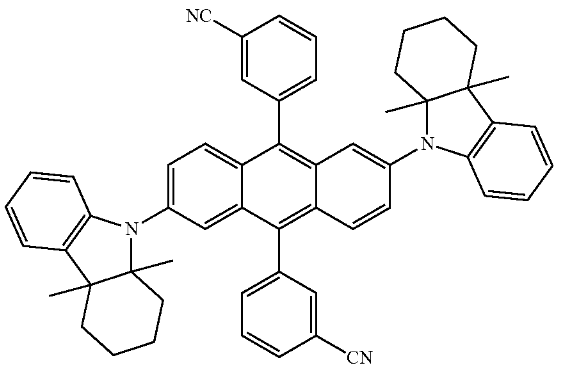
<Compound 137>
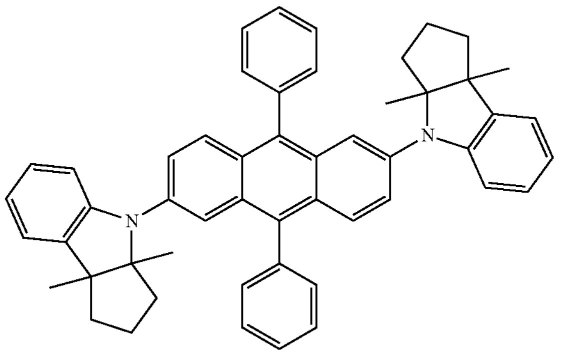
<Compound 138>
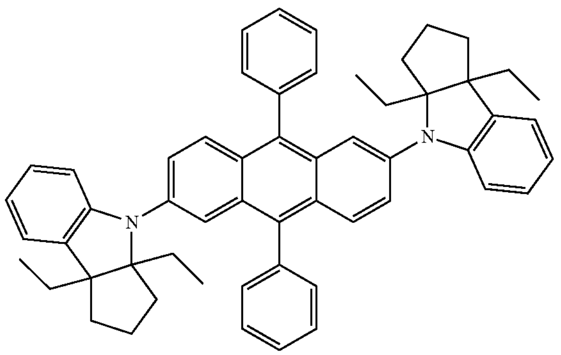
<Compound 139>
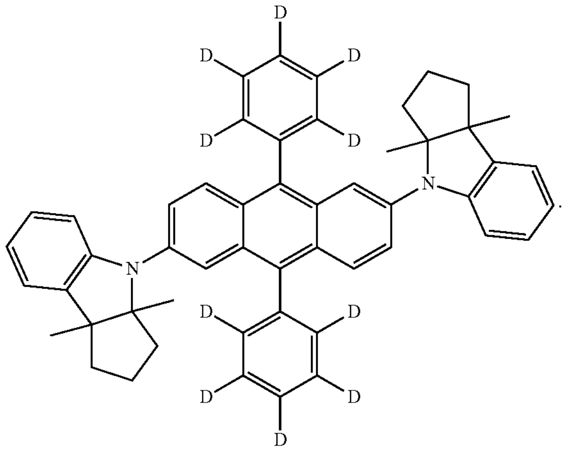
.

5. The organic light-emitting diode of claim 1, further comprising a hole injection layer between the anode and the hole transport layer and an electron injection layer between the electron transport layer and the cathode.

6. The organic light-emitting diode of claim 5, wherein at least one of the layers are formed using a deposition process or a solution process.

7. The organic light-emitting diode of claim 1, wherein the organic light-emitting diode is used for a device selected from among a flat display device, a flexible display device, a monochrome or grayscale flat illumination device, and a monochrome or grayscale flexible illumination device.

* * * * *